United States Patent [19]

Kimachi et al.

[11] Patent Number: 5,785,968
[45] Date of Patent: Jul. 28, 1998

[54] ANTI-FELINE CALICIVIRUS RECOMBINANT ANTIBODY AND GENE FRAGMENT ENCODING THE SAME

[75] Inventors: Kazuhiko Kimachi; Hiroaki Maeda, both of Kumamoto; Kiyoto Nishiyama, Kikuchi; Sachio Tokiyoshi, Kumamoto; Yukinobu Tohya, Bunkyo-ku; Takeshi Mikami, Kamagaya, all of Japan

[73] Assignee: Juridical Foundation The Chemo-Sero-Therapeutic Research Institute, Kumamoto, Japan

[21] Appl. No.: 24,253

[22] Filed: Mar. 1, 1993

[30] Foreign Application Priority Data

Feb. 28, 1992 [JP] Japan ..................... 4-079189

[51] Int. Cl.$^6$ ............. C07H 21/04; C07H 16/00; A61K 39/395
[52] U.S. Cl. ............. 424/147.1; 530/389.4; 424/159.1; 424/133.1; 536/23.53
[58] Field of Search ............. 530/389.4; 536/23.53; 424/85.8, 133.1, 159.1, 147.1

[56] References Cited

U.S. PATENT DOCUMENTS

| | | | |
|---|---|---|---|
| 3,937,812 | 2/1976 | Bittle et al. | 424/186.1 |
| 3,944,469 | 3/1976 | Bittle et al. | 424/186.1 |

FOREIGN PATENT DOCUMENTS

| | | |
|---|---|---|
| 417486A | 3/1991 | European Pat. Off. |
| 9101332 | 2/1991 | WIPO |

OTHER PUBLICATIONS

Man Sung Co et al., "Humanized Antibodies for Antiviral Therapy," Proc. Natl. Acad. Sci. USA, vol. 88, No. 7, pp. 2869–2873, Apr. 1991.

Vernon T. Oi et al., "Chimeric Antibodies," Biotechniques, vol. 4, No. 3, pp. 214–221 (1986).

Queen et. al. PNAS. 86: 10029 1989.

Tohya et. al. Arch Virol 117 (3–4) 1991 173–182.

*Primary Examiner*—Lila Feisee
*Attorney, Agent, or Firm*—Foley & Lardner

[57] ABSTRACT

Anti-FCV (feline calicivirus) feline-type recombinant antibody effective for treatment, prevention and diagnosis of FCV infection and a gene fragment useful for preparation of said antibody are provided. Cell line 1D7 capable of producing a mouse monoclonal antibody having an excellent FCV-neutralizing activity was constructed and a gene fragment coding for the V region in charge of the FCV-specific binding of said antibody was obtained. This gene fragment and the gene coding for the constant region of the feline antibody are used to give a chimeric anti-FCV recombinant antibody. The obtained recombinant antibody is a novel antibody and is useful for the diagnosis, treatment and prevention of feline virus infections, particularly feline calicivirus infection, with high safety in administration into cats.

3 Claims, 14 Drawing Sheets

M : Molecular weight marker
H : H chain gene
L : L chain gene

FIG. 3

AAGCTTGCCGCCACC
HindIII

| Leader                                                                                          60 | FR1
MetLysCysSerTrpValIlePhePheLeuMetAlaValValThrGlyValAsnSerGlu
ATGAAATGCAGCTGGGTTATCTTCTTCCTGATGGCAGTGGTTACAGGGGTCAATTCAGAG
   (MHL74)

FR1                                                                                       120
ValGlnLeuGlnGlnSerGlyAlaGluLeuValLysProGlyAlaSerValArgLeuSer
GTTCAGCTGCAGCAGTCTGGGGCAGAACTTGTGAAGCCAGGGGCCTCAGTCAGGTTGTCC

FR1            |      CDR1       |      FR2            180
CysThrAlaSerGlyPheAsnIleLysAspThrTyrMetHisTrpValLysGlnArgPro
TGTACAGCTTCTGGCTTCAACATTAAAGACACCTATATGCACTGGGTGAAACAGAGGCCT

FR2                      |             CDR2           240
GluGlnGlyLeuGluTrpIleGlyArgIleAspProAlaAsnGlyAsnThrLysTyrAsp
GAACAGGGCCTGGAGTGGATTGGAAGGATTGATCCTGCAAATGGTAATACTAAATATGAC

CDR2             |             FR3                    300
ProArgPheGlnGlyLysAlaThrIleThrAlaAspThrSerPheAsnThrAlaTyrLeu
CCGAGGTTCCAGGGCAAGGCCACTATAACAGCAGACACATCCTTCAACACAGCCTACCTG

FR3                  | CDR3   360
GlnValAsnSerLeuThrSerGluAspThrAlaValTyrTyrCysAlaSerGlyGlyAsn
CAAGTCAACAGCCTGACATCTGAGGACACTGCCGTCTATTACTGTGCTAGCGGGGGTAAT

CDR3       |              FR4              |         400
AlaTrpLeuAlaTyrTrpGlyGlnGlyThrLeuValThrValSerAla
GCCTGGCTTGCTTACTGGGGCCAAGGGACTCTGGTCACTGTCTCTGCAGGTGAGTGGATCC
    JH3                                       (MJH3)       BamHI

⁓⁓⁓⁓ : Primer

FIG. 4

```
                                                AAGCTTGCCGCCACC
                                                ───────────────
                                                HindIII
 | Leader                                                    60
ATGAGTGTGCTCACTCAGGTGCTGGCGTGGCTGCTGCTGTGGCTTACAGGTGCCAGATGT
MetSerValLeuThrGlnValLeuAlaTrpLeuLeuLeuTrpLeuThrGlyAlaArgCys

|         FR1                                              120
GACATCCAGATGACTCAGTCTCCAGCCTCCCTATCTGCATCTGTGGGAGAAACTGTCACC
AspIleGlnMetThrGlnSerProAlaSerLeuSerAlaSerValGlyGluThrValThr

FR1    |           CDR1              |     FR2           180
ATCACATGTCGAGCAAGTGGGAATATTCACAATTATTTAGCATGGTATCAGAAGAAACAG
IleThrCysArgAlaSerGlyAsnIleHisAsnTyrLeuAlaTrpTyrGlnLysLysGln

FR2        |         CDR2        | FR3           240
GGAAAATCTCCTCAGCTCCTGGTCTATAGTGCAGAAAGTTTAGCAGTTGGTGTGCCATCA
GlyLysSerProGlnLeuLeuValTyrSerAlaGluSerLeuAlaValGlyValProSer

FR3                                300
AGGTTCAGTGGCAGTGGATCAGAAACACACTATTTTCTCAAGATCGACAGCCTGCAGCCT
ArgPheSerGlySerGlySerGluThrHisTyrPheLeuLysIleAspSerLeuGlnPro

FR3              |          CDR3          | FR4  360
GAAGATTTTGGGAGTTATTACTGTCAAAATTTTTGGACTACTCCGTGGACGTTCGGTGGA
GluAspPheGlySerTyrTyrCysGlnAsnPheTrpThrThrProTrpThrPheGlyGly
                                                       Jκ1

FR4              |
GGCACCAAGCTGGAGCTGAAACGTAAGTGGATCC
                                ─────
GlyThrLysLeuGluLeuLysArg
        (MJK1)              BamHI

──⌇⌇⌇⌇──  : Primer
```

FIG. 5

```
           |   Leader         |          FR1                  |CDR1|  FR2      60
     1 D 7  MKCSWVIFFLMAVVTGVNSEVQLQQSGAELVKPGASVRLSCTASGFNIKDTYMHWVKQRP

******.*********************.*****.********************
Antibody 1  MKCSWVMFFLMAVVTGVNSEVQLQQSGAELVRPGASVKLSCTASGFNIKDTYMHWVKQRP
            **********************************.*****.********************
Antibody 2  MKCSWVIFFLMAVVTGVNSEVQLQQSGAELVRPGASVKLSCTASGFNIKDTYMHWVKQRP
            *************.*****************.*****.***********.********
Antibody 3  MKCSWVIFFLMAVVIGVNSEVQLQQSGAELVRPGASVKLSCTASGFNIKDDYMHWVKQRP
            ******************************.*****.********************
Antibody 4  MKCSWVIFFLMAVVTGVNSEVQLQQSGAELVRPGASVKLSCTASGFNIKDTYMHWVKQRP
            ******.*******************  ****.*****************.********
Antibody 5  MKCSWVMFFLMAVVTGVNSEVQLQQSVAELVRPGASVRLSCTASGFNIKNTYMHWVKQRP

|  CDR2          |       FR3              | CDR3
     1 D 7  EQGLEWIGRIDPANGNTKYDPRFQGKATITADTSFNTAYLQVNSLTSEDTAVYYCAS--G

***********************.************ ******..**************
Antibody 1  EQGLEWIGRIDPANGNTKYDPKFQGKATITADTSSNTAYLQLSSLTSEDTAVYYCASYRY
            ********** ********.************ ******..*************
Antibody 2  EQGLEWIGRIDLANGNTKYDPKFQGKATITADTSSNTAYLQLSSLTSEDTAVYYCARYYRY
            ********.***.**.*.*...******.***** **.***..************..*.
Antibody 3  EQGLEWIGWIDPENGDTQYASKFQGKATMTADTSSNTTYLQLSSLTSEDTAVYYCTTYGA
            ********** ********.************ ******..*************
Antibody 4  EQGLEWIGRIDLANGNTKYDPKFQGKATITADTSSNTAYLQLSSLTSEDTAVYYCARYYRY
            ****************.*.** ********* ******..*******.****.
Antibody 5  EQGLEWIGRIDPANGNTKYAPKFQVKATITADTSSNTAYLQLSSLTSEDTAIYYCAPYYY

| FR4      136
     1 D 7  GNAWLAYWGQGTLVTVSAA

..**.*************
Antibody 1  ERAWFAYWGQGTLVTVSA
            ..****** ****.
Antibody 2  PYYAMDYWGQGTSVTVSS
            ****** ****.
Antibody 3    YAMDYWGQGTSVTVSS
            ..****** ****.
Antibody 4  PYYAMDYWGQGTSVTVSSESQSFPNVF
            .....**.** ****.
Antibody 5  GGYFDVWGAGTTVTVSS
```

FIG. 6

```
             |    Leader     |       FR1            |   CDR1    |  FR2   60
     1 D 7  MSVLTQVLAWLLLWLTGARCDIQMTQSPASLSASVGETVTITCRASGNIHNYLAWYQKKQ

***.****..******.***************.****.********.**...*****.**
Antibody A  MSVPTQVLGLLLLWLTDARCDIQMTQSPASLSVSVGESVTITCRASENIYSNLAWYQQKQ
             ********.***********************************************.**
Antibody B  MSVLTQVLALLLLWLTGARCDIQMTQSPASLSASVGETVTITCRASGNIHNYLAWYQQKQ
             ********.***********************************************.**
Antibody C  MSVLTQVLALLLLWLTGARCDIQMTQSPASLSASVGETVTITCRASGNIHNYLAWYQQKQ
                             **************.*********.**..******.**
Antibody D                  DIQMTQSPASLSASVG-TVTITCRASENIYSYLAWYQQKQ
             ***.****..******.*.********************.****.**..******.**
Antibody E  MSVPTQVLGLLLLWLTGVRCDIQMTQSPASLSASVGETVTIICRASVNIYSYLAWYQQKQ FR2    | CDR2 |         FR3                | CDR3  | FR4
     1 D 7  GKSPQLLVYSAESLAVGVPSRFSGSGSETHYFLKIDSLQPEDFGSYYCQNFWTT-PWTFGG

*********.*..*..***********.*.*.***.***.*********.**.*.*.***
Antibody A  GKSPQLLVYVATKLVDGVPSRFSGSGSGTQYSLKINSLQSEDFGSYYCQHFWDT-PFTFGS
             *********.*..**.***********.*.*.***.************.****.******
Antibody B  GKSPQLLVYNAKTLADGVPSRFSGSGSGTQYSLKINSLQPEDFGSYYCQHFWTTPPWTFGG
             *********.*..**.***********.*..***.*************.**.**      *
Antibody C  GKSPQLLVYNAKTLADGVPSRFSGSGSGTQYSLKINSLQPEDFGSYYCQHFWSTP       G
             *********.*..**.***********.*..***.*************...*.*.***.
Antibody D  GKSPQLLVYNAKTLAEGVPSRFSGSGSGTQFSLKINSLQPEDFGSYYCQHHYVT-PYTFGS
             *********.*..**.***********.*..***.************..*.***
Antibody E  GKSPQLLVYNAKILAEGVPSRFSGSGSGTQFSLKINSLQPEDFGSYYCQHHY-GPFTFG 126
     1 D 7  GTKLELKR

*****.**
Antibody A  GTKLEMKR
             *****.*
Antibody B  GTKLEIK
             *****
Antibody C  GTKLE
             *****.*
Antibody D  GTKLEIK
```

Lane 1: Molecular weight marker
Under reductive condition
Lane 2: P 3.6.5.3 culture supernatant
Lane 3: Chimeric antibody (F1D7)
Lane 4: Feline polyclonal antibody
Under non-reductive condition
Lane 5: P 3.6.5.3 culture supernatant
Lane 6: Chimeric antibody (F1D7)
Lane 7: Feline polyclonal antibody

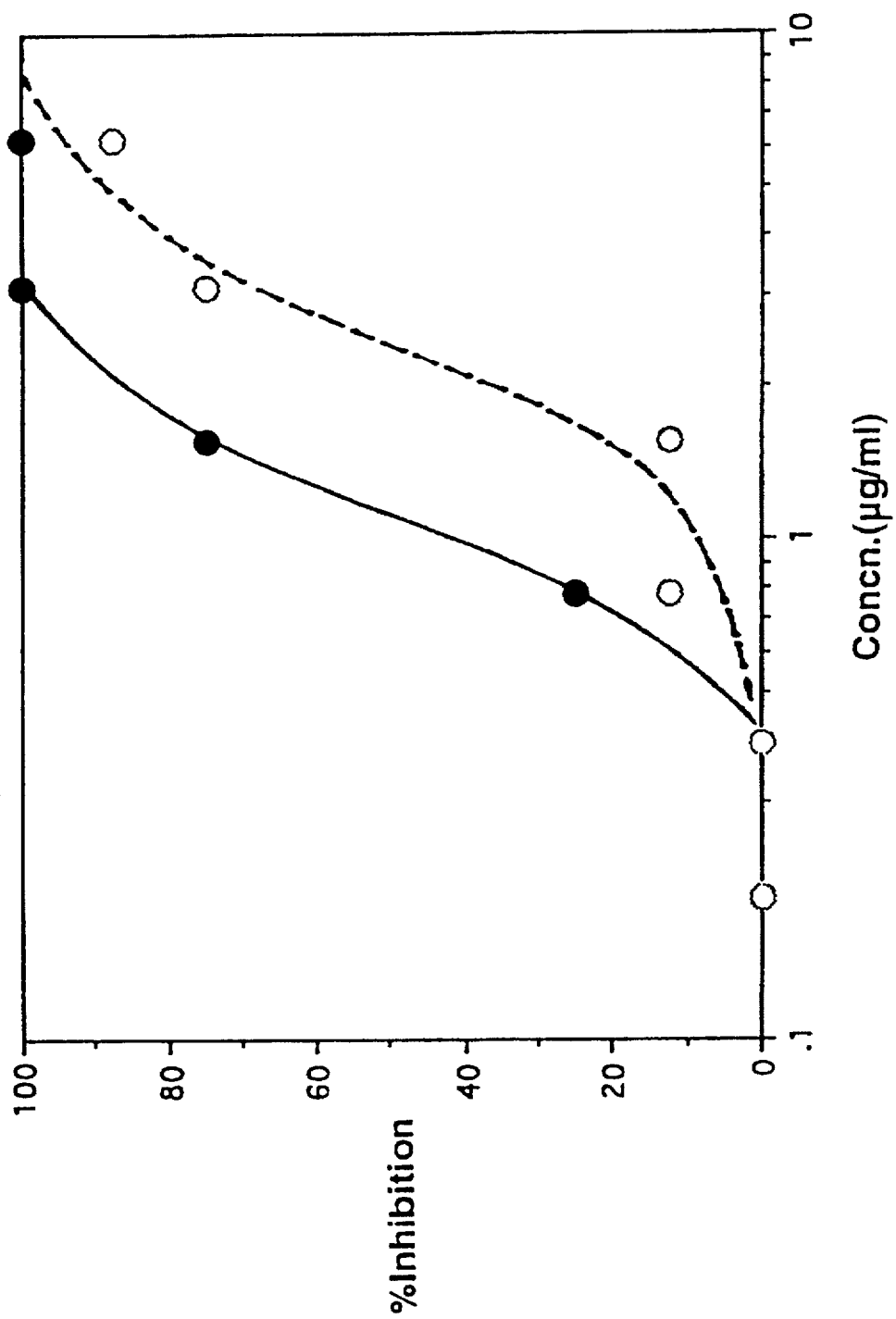

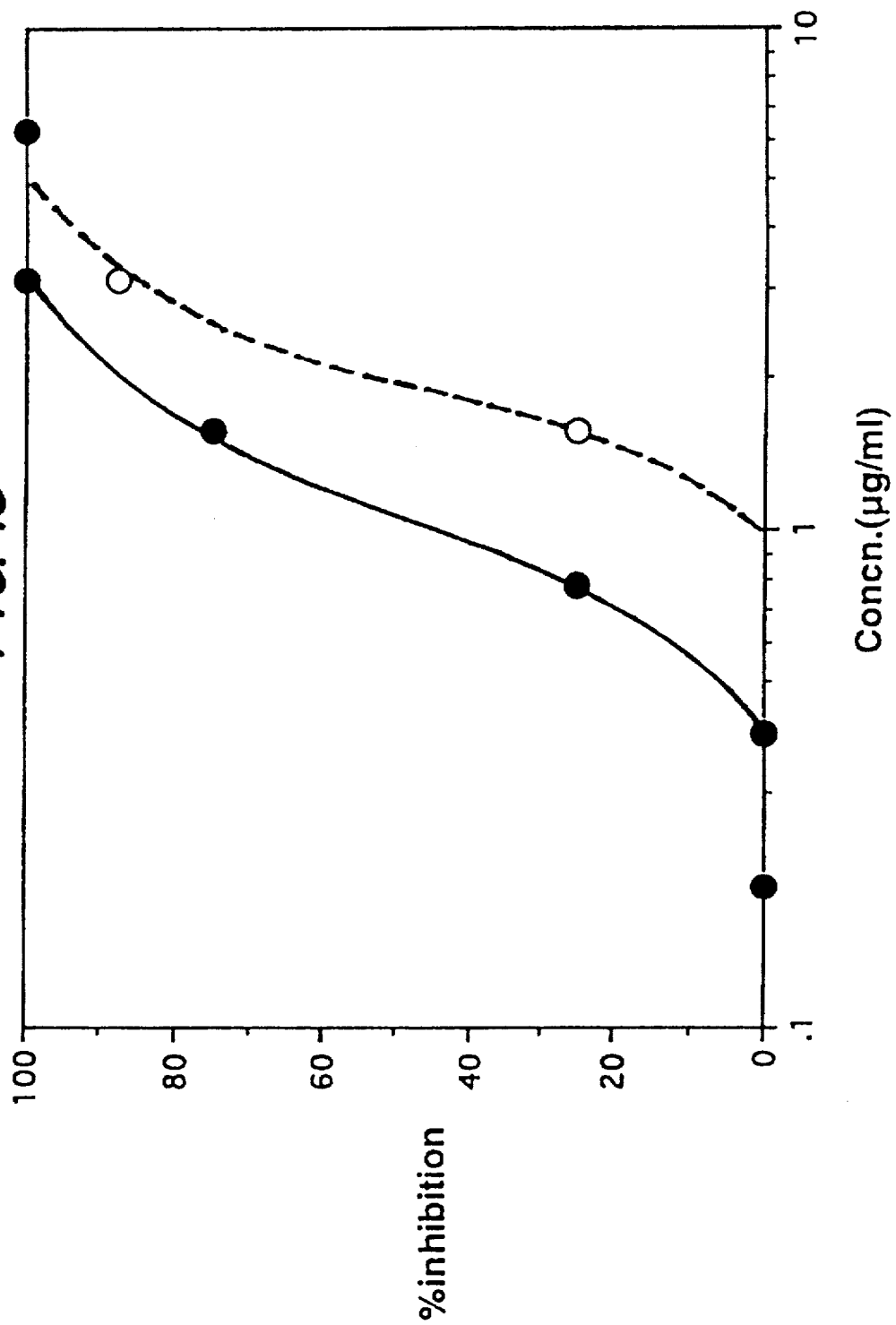

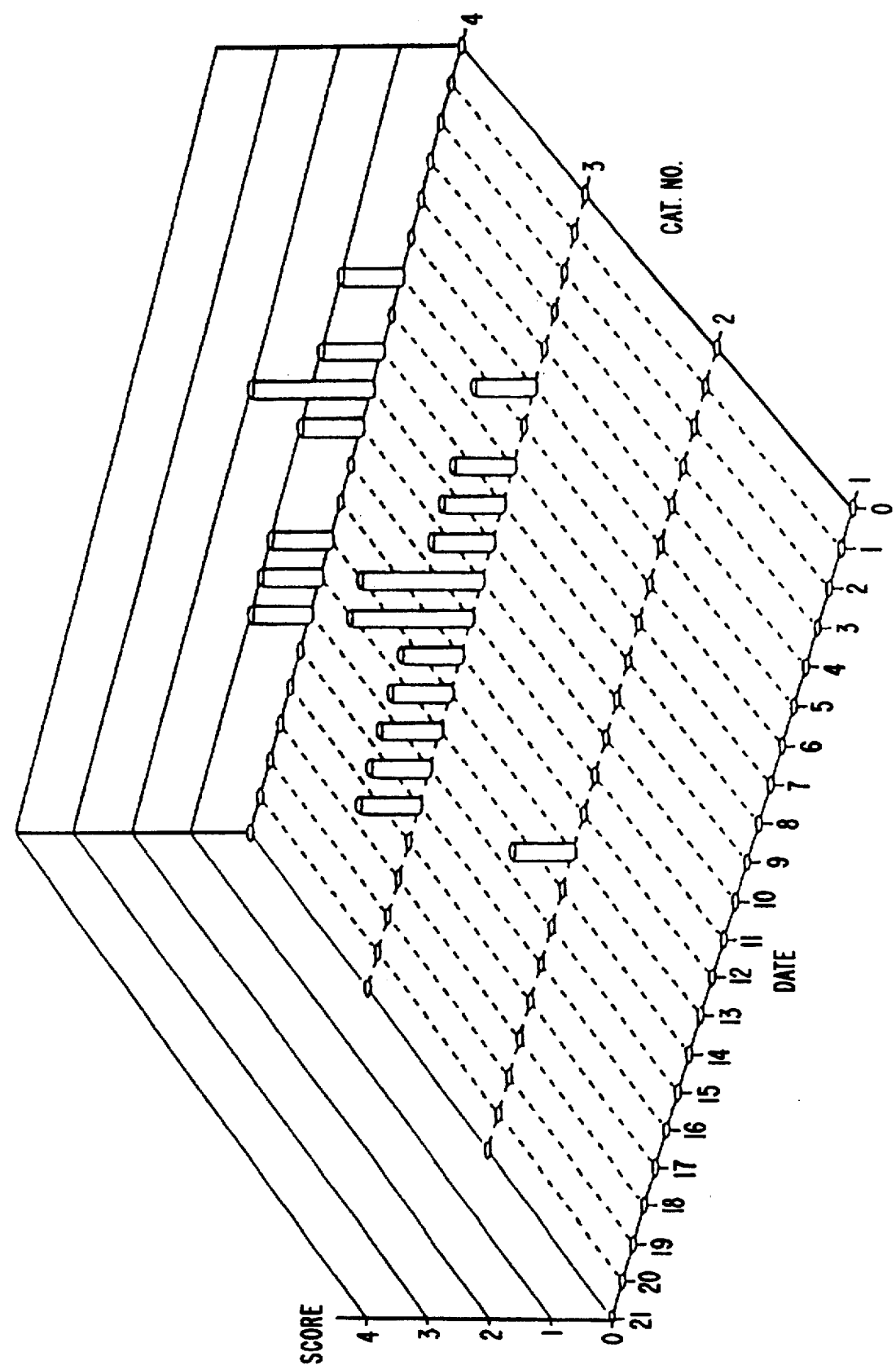

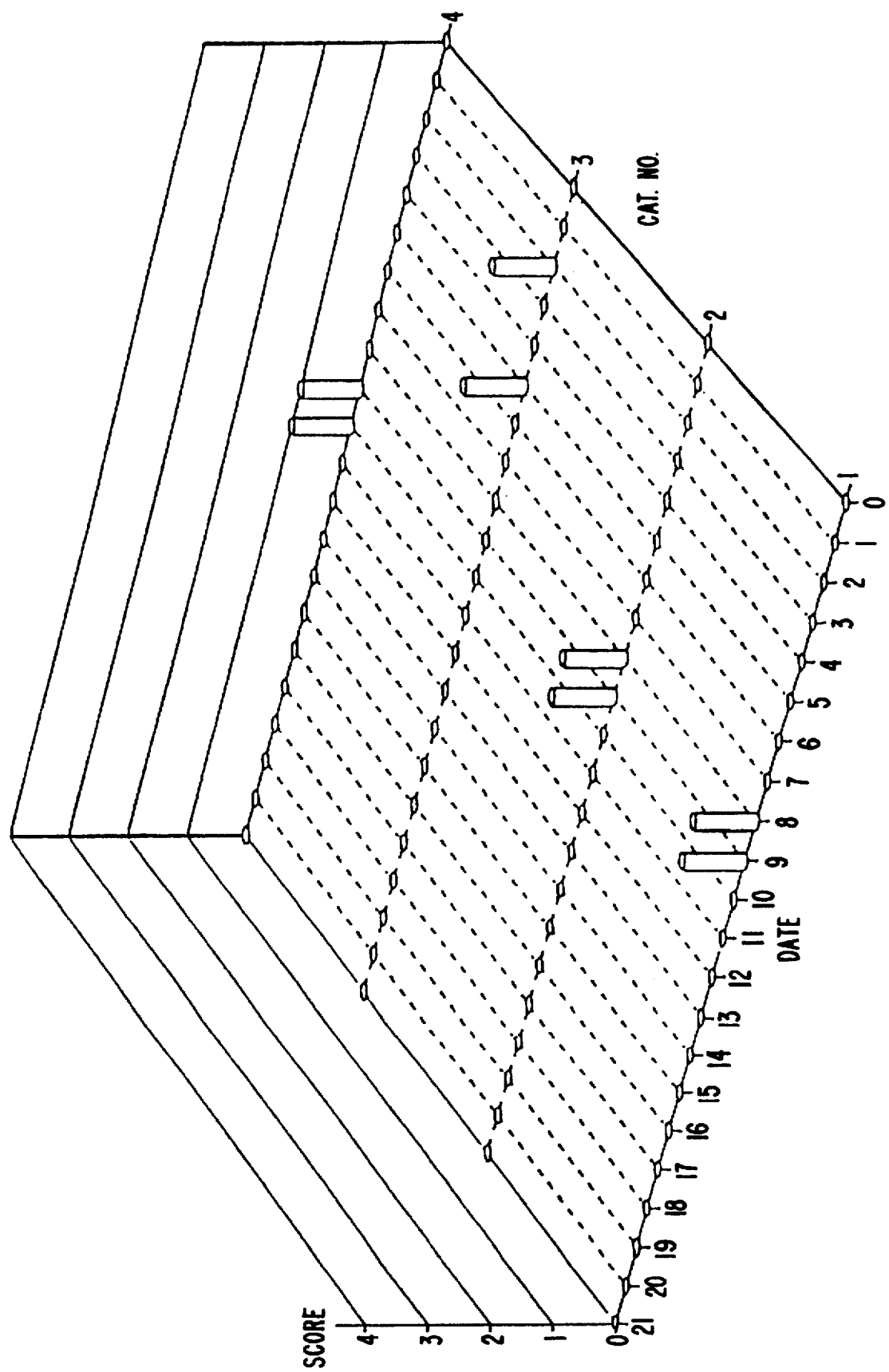

ANTI-FELINE CALICIVIRUS RECOMBINANT ANTIBODY AND GENE FRAGMENT ENCODING THE SAME

The present invention relates to a novel feline monoclonal antibody useful for diagnosis, treatment and prevention of feline calicivirus infection (hereinafter, the feline calicivirus is referred to as "FCV", and the feline calicivirus infection is referred to as "FCI"). More particularly, the present invention relates to a feline-type anti-FCV recombinant antibody which is prepared by replacing the constant region of a mouse-type anti-FCV neutralizing monoclonal antibody with the constant region of a feline antibody, and a gene fragment coding for said antibody.

PRIOR ART

From ancient times, cats have been favorably treated as a pet by human. In modern Europe and America, they are called "Companion species" and now becoming a member of human society. On the other hand, cats have hitherto made a great contribution to human as an experimental animal in various fields including medicine, pharmacy, animal husbandry, veterinary science, psychology, etc. In recent years, they make further contribution as the so-called "SPF Cat (specific-pathogen free cat)" in tests for determination of effect and safety of drugs, and hence, usefulness thereof for human becoming greater and greater. In any event, it is important to obtain reliable knowledge of feline diseases, especially feline infectious diseases, and to establish a method for more certain diagnosis, treatment and prevention of said feline diseases.

There are many feline diseases caused by viral infection. Among them, the infectious diseases of upper respiratory that is caused by FCV is an acute disease having a high lethality rate. No specific agent for treating the diseases has been developed yet, and only symptomatic therapy with antibiotics, sulfamides, etc. is available for preventing secondary bacterial infections, and hence, the conventional methods for treating the feline viral infections are still insufficient.

On the other hand, although an attenuated vaccine and an inactivated vaccine have been used for prevention of the viral infectious diseases, the conventional vaccines have not been effective for preventing these diseases, particularly in the infection of FCV, because there are a variety of serotype viral strains of FCV and further it is difficult to determine the timing of initial inoculation due to insufficient clarification of the maternal immunity. Thus, it is earnestly desired to develop a new vaccine which is more effective for preventing these diseases.

Calicivirus is known to grow topically (in the upper respiratory tract). With calicivirus, continuous viral infection is exhibited in spite of a high level of neutralizing antibody titer in feline blood, and further there are a variety of serotypes of this virus, and hence, the treatment with antibodies has been deemed to be ineffective.

As mentioned above, there are many serotypes in FCV. Under the circumstances, several neutralizing mouse monoclonal antibodies against FCV have been established (M. J. Capter et al., J. Gen. Virol., 70, 2197, 1989), but most of these conventional neutralizing antibodies could neutralize only a specific serotype of FCVs, i.e. they had a narrow neutralizing spectrum. Even if such mouse monoclonal antibodies having a narrow neutralizing spectrum are administered to animal patients, the diseases will not be effectively treated.

In addition, all of the hitherto established monoclonal antibodies are those derived from mouse hybridomas. However, when these mouse-derived monoclonal antibodies are administered to cats, they are recognized as a heterologous protein, and as a result, various side effects such as anaphylactic shock or serum sickness are provoked or a half life of the activity is shortened, and hence, the treatment efficiency of the antibodies is lowered. Therefore, the conventional mouse monoclonal antibodies have never given satisfactory effects. In addition, such mouse monoclonal antibodies may not be effective in interacting with feline effector cells or effector molecules such as complement.

Under the circumstances, the present inventors have intensively studied to find a monoclonal antibody which can neutralize various FCV strains and is widely useful for the prevention and treatment of FCI, and have established a mouse monoclonal antibody 1D7 capable of neutralizing various FCV strains, determined a nucleotide sequence coding for a variable region (V region) of said antibody, and found a specific amino acid sequence in the V region closely related to the FCV neutralization of said antibody. Furthermore, the present inventors have constructed a vector expressing an anti-FCV chimeric antibody having FCV-neutralizing activity by linking the gene fragment coding for the V region of said FCV-neutralizing antibody to a gene fragment coding for the constant region of a feline antibody which has previously been found by the present inventors, and have expressed said constructed vector to give the anti-FCV chimeric antibody. In addition, the feline-type antibody of the present invention was tested to treat FCV-infected cats, and as a result, it was found that the antibody of the present invention showed an unexpectedly excellent effect to treat the FCV infection.

SUMMARY DESCRIPTION OF THE INVENTION

An object of the invention is to provide a novel anti-FCV feline chimeric antibody which is prepared by replacing the constant region of the mouse monoclonal antibody with the constant region of the feline antibody using the genetic engineering technique. Another object of the invention is to provide a gene fragment coding for said antibody useful for preparation of said antibody. A further object of the invention is to provide an agent for treating FCV infection comprising said feline-type chimeric antibody. These and other objects and advantages of the invention will be apparent to those skilled in the art from the following description.

BRIEF DESCRIPTION OF DRAWING

FIG. 3 shows the nucleotide sequence of the VH gene obtained in Example (3) and the amino acid sequence coded by said nucleotide sequence.

FIG. 4 shows the nucleotide sequence of the Vκ gene obtained in Example (4) and the amino acid sequence coded by said nucleotide sequence.

FIG. 5 shows homological comparison of amino acid sequences of the VH region of the antibody 1D7 and antibodies 1 to 5.

FIG. 6 shows homological comparison of amino acid sequences of the Vκ region of the antibody 1D7 and antibodies A to E.

FIG. 12 is a graph showing the neutralization of FCV by F1D7 antibody in the presence and absence of feline complement.

FIG. 13 is a graph showing the neutralization of FCV by felinized chimeric antibody F1D7 and mouse antibody 1D7 in the presence of feline complement.

DETAILED DESCRIPTION OF THE INVENTION

Although FCV-neutralizing monoclonal antibodies have been established in several laboratories, any monoclonal antibody having a broad virus-neutralizing spectrum has not yet been reported. Therefore, in order to obtain such a monoclonal antibody having a broad neutralizing spectrum, the present inventors have prepared hybridomas by cell fusion of lymphocytes derived from mouse immunized with FCV-F4 viral particle with mouse myeloma cells in a usual manner. Cloning has been conducted on the culture supernatant of the obtained hybridomas based on the ability to neutralize virus and thereby an antibody-producing cell 1D7 which produces a monoclonal antibody showing a quite excellent FCV-neutralizing activity has been established.

The monoclonal antibody produced by this cell could neutralize a variety of FCV strains. This monoclonal antibody could also neutralize those viruses which acquired tolerance against other neutralizing monoclonal antibodies, and hence, it has been found that this antibody is an excellent monoclonal antibody having a broad virus-neutralizing spectrum.

In general, it is known that the specificities of an antibody such as virus-neutralizing activity are determined by an amino acid sequence of the variable (V) region of an antibody which binds to an antigen. In this sense, the present inventors have investigated an amino acid sequence of the V region of the antibody 1D7. The amino acid sequence has been determined by cloning a gene coding for the V region of the antibody and determining the nucleotide sequence thereof. As a result, it has been found that the V region has amino acid sequences shown in FIGS. 3 and 4.

Figure 1:
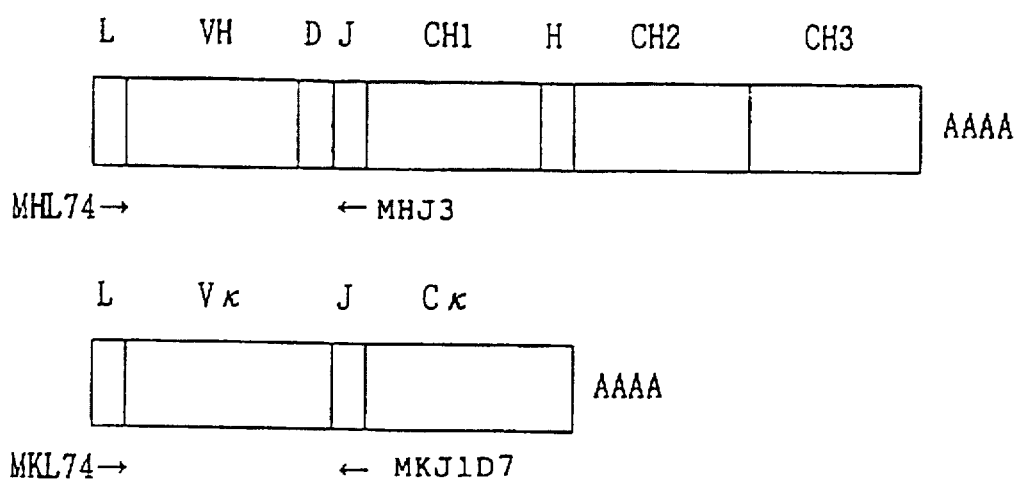
FIG. 1 illustrates the structure of a gene (cDNA) coding for an H chain (the upper) and an L chain (the lower) of an antibody.

As illustrated in FIG. 1, the antibody H chain gene generally contains about 200 VH genes, about 10 D genes, and 4 JH genes while the L(κ) chain gene contains about 200 Vκ genes, and 4 J genes. During differentiation of B cells, each one gene is selected from these V(D)J gene fragments and they are reconstituted to form a gene coding for a whole variable region. The diversity of the variable region of antibody is further increased by addition of the N sequence, somatic mutation, etc. It has been found that the gene coding for the variable region of 1D7 according to the present invention is the only one selected from the above diversity and that the specific virus-neutralizing activity of 1D7 is due to the specific amino acid sequence coded by said gene.

In order to investigate which part of said amino sequence is the most specific to the 1D7 antibody, the amino acid sequence was compared between the variable regions of the 1D7 antibody and of several known antibodies (antibodies 1 to 5 and antibodies A to E)(FIGS. 5 and 6). As a result, the following two amino acid sequences have been found to be specific to 1D7.

(1) Gly Gly Asn Ala Trp Leu (SEQ ID NO: 11) (H chain CDR3 region)

(2) Ser Ala Glu Ser Leu Ala Val (SEQ ID NO: 12) (L chain CDR2 region)

The above specific sequences (1) and (2) were found in a region called Complementarity Determining Region (hereinafter referred to as "CDR") which actually reacts with an antigen. It has been found that these CDRs provide a specific antigen-binding activity, in most cases, only by the combination of the amino acid sequences, and moreover, only by the combination of the H chain and the L chain. In other words, even if there is any antibody having amino acid sequences with a high homology of the V region as a whole, it will probably show a different specificity unless these CDRs are identical. Accordingly, the above amino acid sequences (1) and (2) are closely related to the binding with FCV and the neutralizing activity of the antibody. This has firstly been found by the present inventors by isolating the gene coding for the variable region of 1D7. Furthermore, the determination of the nucleotide sequence and the amino acid sequence of the V region of 1D7 makes it possible to further improve the antigen-binding activity of the antibody or to change the V region itself of the antibody into a V region of feline antibody by modifying in part the determined nucleotide sequence or the amino acid sequence. An antibody or a peptide having such an amino acid sequence is expected to be useful for treatment, diagnosis or prevention of FCI.

That is, the gene fragment coding for the V region of the antibody having a neutralizing activity against FCV of the present invention has the following characteristic features.

The gene fragment coding for VH or a part of VH of the antibody capable of specifically reacting with FCV of the present invention is a gene fragment coding for VH region of the antibody wherein the nucleotide sequence coding for CDR3 of said antibody is a nucleotide sequence coding for the following amino acid sequence:

Gly Gly Asn Ala Trp Leu (SEQ ID NO: 11)

Preferable VH gene fragment comprising such a nucleotide sequence coding for the above amino acid sequence of the present invention includes a VH gene fragment wherein nucleotide sequences coding for CDRs 1 to 3 are nucleotide sequences coding for the following amino acid sequences:

CDR1: Asn Ile Lys Asp Thr Tyr Met His (SEQ ID NO: 13)

CDR2: Arg Ile Asp Pro Ala Asn Gly Asn Thr Lys Tyr Asp Pro Arg Phe Gln Gly Lys (SEQ ID NO: 14)

CDR3: Gly Gly Asn Ala Trp Leu Ala Tyr (SEQ ID NO: 15)

Preferable nucleotide sequences of the above-mentioned VH gene fragment include nucleotide sequences coding for the amino acid sequence shown in the Sequence Listing as SQ ID NO: 1. One example of such preferable nucleotide sequences is that shown in the Sequence Listing as SQ ID NO: 1.

On the other hand, a gene fragment coding for VL or a part of VL of the antibody capable of specifically reacting with FCV of the present invention is a gene fragment coding for the VL region of the antibody wherein the nucleotide sequence coding for CDR2 of said antibody is a nucleotide sequence coding for the following amino acid sequence:

Ser Ala Glu Ser Leu Ala Val (SEQ ID NO: 17)

Preferable VL gene fragment comprising such a nucleotide sequence coding for the above amino acid sequence of the present invention includes a VL gene fragment wherein nucleotide sequences coding for CDRs 1 to 3 are nucleotide sequences coding for the following amino acid sequences:

CDR1: Arg Ala Ser Gly Asn Ile His Asn Tyr Leu Ala (SEQ ID NO: 16)

CDR2: Ser Ala Glu Ser Leu Ala Val (SEQ ID NO: 17)

CDR3: Gln Asn Phe Trp Thr Thr Pro Trp Thr (SEQ ID NO: 18)

Preferable nucleotide sequences of the above-mentioned VL gene fragment include nucleotide sequences coding for the amino acid sequence shown in the Sequence Listing as SQ ID NO: 2. One example of such preferable nucleotide sequences is that shown in the Sequence Listing as SQ ID NO: 2.

It is not preferable to directly administer the mouse-type antibody 1D7 to cats for treatment of FCI because of side effects, shortening of half life, and the like. This is because the antibody itself is mouse-derived, and hence, when it is introduced into cats for treatment, it is recognized as a foreign antigen and acts as an immunogen. Therefore, for use as a medicament, it is necessary to prevent the immunogenicity of the antibody. It is known that the immunogenicity of the antibody molecule is mainly provoked by a constant (C) region of the antibody. It is also understood that the V region and the C region are functionally independent, and hence, the specificity of an antibody with an antigen is not affected by replacement of the C region with that derived from another animal species. In this context, the present inventors have replaced the constant region of the mouse-type 1D7 with that derived from cats by using the genetic engineering technique to prepare a feline-type 1D7.

The feline-type anti-FCV chimeric antibody 1D7 can be prepared by constructing a structural gene coding for an H chain or an L chain of a feline-type chimeric antibody by linking the gene coding for the constant region of a feline antibody (CH gene or CL gene) to the downstream (3' site) of the gene coding for VH or VL of the anti-FCV antibody of the present invention (VH gene or VL gene) and expressing the thus prepared structural gene in a suitable animal cell to give a desired anti-FCV chimeric antibody.

The gene coding for the constant region of a feline antibody has already been found by the present inventors (cf. EP 417486A). The gene coding for the constant region of a feline antibody includes a gene fragment coding for CH including those coding for the amino acid sequence shown in the Sequence Listing as SQ ID NO: 3, specific example being the nucleotide sequence shown in the Sequence Listing as SQ ID NO: 3; a gene fragment coding for Cκ including those coding for the amino acid sequence shown in the Sequence Listing as SQ ID NO: 4, specific example being the nucleotide sequence shown in the Sequence Listing as SQ ID NO: 4; and a gene fragment coding for Cλ including those coding for the amino acid sequence shown in the Sequence Listing as SQ ID NO: 5, specific example being the nucleotide sequence shown in the Sequence Listing as SQ ID NO: 5.

In addition to the preparation of the above-mentioned chimeric antibody wherein the V region is derived from mice and the C region is derived from cats, the gene fragment coding for the V region of the antibody having a neutralizing activity against FCV can also be used for preparing a modified antibody wherein a frame region (FR) of the V region is also replaced with that of antibodies derived from animals other than mice (in case of the present invention, antibodies from cats). Hitherto, a whole amino acid sequence of general FR of the V region of feline antibodies has not yet been reported, but parts of said sequence have already been reported (KEHO J. M. et al., Proc. Nat. Acad. Sci., 69, 2052, 1972). Using a suitable primer prepared based on the above known sequences and the amino acid sequences of the constant region of feline antibodies, which sequences the present inventors have previously determined, a gene coding for the V region of feline antibodies can be cloned to make it possible to determine the amino acid sequence of said FR region. The modified antibody can be prepared basically in accordance with the known methods (e.g. EP 239400A). The gene fragment of the present invention used for preparing the modified antibody comprises, as a part of genes coding for the VH chain and the VL chain, nucleotide sequences coding for the following amino acid sequences:

VH chain: Gly Gly Asn Ala Trp Leu (SEQ ID NO: 11)

VL chain: Ser Ala Glu Ser Leu Ala Val (SEQ ID NO: 12)

Preferably, the gene fragment of the present invention comprises, as gene segments coding for CDRs of the V region of said modified antibody, nucleotide sequences coding for the following amino acid sequences:

VH chain:

CDR1: Asn Ile Lys Asp Thr Tyr Met His (SEQ ID NO: 13)

CDR2: Arg Ile Asp Pro Ala Asn Gly Asn Thr Lys Tyr Asp Pro Arg Phe Gln Gly Lys (SEQ ID NO: 14)

CDR3: Gly Gly Asn Ala Trp Leu Ala Tyr (SEQ ID NO: 15)

VL chain:

CDR1: Arg Ala Ser Gly Asn Ile His Asn Tyr Leu Ala (SEQ ID NO: 16)

CDR2: Ser Ala Glu Ser Leu Ala Val (SEQ ID NO: 17)

CDR3: Gln Asn Phe Trp Thr Thr Pro Trp Thr (SEQ ID NO: 18)

In addition, the present inventors have also found that a modified antibody having an excellent specificity of the original mouse-derived monoclonal antibody may be prepared by conducting the reconstitution in such a way that not only CDRs but also a part of FR regions of the V region neighboring CDRs are composed of mouse-derived sequences, rather than in such a way that only CDRs are composed of mouse-derived sequences. That is, by reconstituting not only CDRs but also a part of FR regions of the V region so as to be composed of mouse-derived sequences by referring to the amino acid sequence shown in FIG. 3 for the VH chain and the amino acid sequence shown in FIG. 4 for the VL chain, respectively, there may be obtained a more excellent modified antibody than the modified antibody wherein only CDRs are composed of mouse-derived sequences.

As mentioned above, a structural gene coding for the V region for the chimeric antibody or the modified antibody is constructed using the gene coding for the variable region of the anti-FCV antibody of the present invention, and the thus constructed gene is then linked to the gene coding for the constant region of feline antibodies which has previously been found by the present inventors to prepare a structural gene coding for a feline-type anti-FCV recombinant antibody, so-called chimeric antibody. This gene is linked to the downstream of a suitable promoter gene and the obtained recombinant gene is expressed in animal cells, etc. to give a recombinant antibody of the present invention. It has been confirmed by the present inventors that the thus obtained recombinant antibody is a feline-type monoclonal antibody having an excellent neutralizing activity of the mouse-type antibody 1D7 and is superior to a mouse-type monoclonal antibody on the neutralizing activity under the presence of complement.

Moreover, the present inventors have done the efficacy test and the safety test for a feline-type monoclonal antibody using SPF cats. As a result, it has been found that a feline-type monoclonal antibody of the present invention was safe without side effects such as an anaphylactic shock and was effective against FCI on the FCV infection model using SPF cats.

Accordingly, the anti-FCV chimeric antibody prepared in accordance with the present invention can be used as a drug for treatment and prevention of FCI in cats.

For the prevention and/or treatment of FCI in cats, the antibody of the present invention is usually administered by parenteral route such as intravenous, subcutaneous or intramuscular injection, or by spraying or applying directly into the upper respiratory tract (e.g. nasal cavity or oropharynx). The antibody is usually used in the form of a preparation in admixture with a conventional carrier or diluent. The preparation is prepared, for example, by purifying the antibody expressed in the cells as mentioned above by a conventional purification method and dissolving the purified antibody in a suitable buffer (e.g. phosphate buffer). The preparation usually contains the antibody in a concentration of 0.1 to 500 mg/ml, preferably 1 to 200 mg/ml. The preparation may further be incorporated by conventional additives such as mannitol (in an amount of 1 to 20% by weight), glycine (in an amount of 0.5 to 5% by weight), and a surfactant (in a slight amount such as 0.01% by weight). The preparation may be put on the market in the form of a solution thus prepared, or in the lyophilized form, which is dissolved in a buffer when used.

The dose of the antibody of the present invention is in the range of 0.1 to 300 mg/kg, preferably 1 to 100 mg/kg, in adult cat. For effecting the desired dosage, the preparation of the present invention as prepared above is usually administered in an amount of 0.1 to 2.5 ml/kg, preferably 0.25 to 1.0 ml/kg.

EXAMPLES

The present invention is illustrated by the following Examples but should not be construed to be limited thereto.

(1) Preparation of hybridoma capable of producing anti-FCV neutralizing monoclonal antibody:

A culture supernatant of FCV-infected CRFK cells was precipitated with ammonium sulfate and the precipitate was dialyzed. It was resuspended in a phosphate buffer and the suspension was administered intraperitoneally to BALB/c mice together with Freund's complete adjuvant to immunize the mice. After two weeks, mouse lymphocytes and mouse myeloma cells (P3U1) were cell-fused with polyethylene glycol to prepare hybridomas. Cloning was conducted on the hybridomas based on the ability of the culture supernatant of hybridomas to neutralize the virus to establish an FCV-neutralizing monoclonal antibody-producing cell, 1D7. The monoclonal antibody produced by this cell could neutralize various FCV strains. Furthermore, it was found that this monoclonal antibody could also neutralize those viruses that acquired tolerance against another neutralizing antibodies, and hence, had a broad virus neutralizing spectrum.

(2) Isolation of a gene coding for the variable region of the anti-FCV antibody (1D7):

Whole RNAs were extracted from 1 to 0.5×10$^7$ cells (hybridomas) and mRNAs were purified with Oligo dT column (manufactured by Stratagene; Poly(A) Quick MRNA Purification Kit). Using a reverse transcriptase (manufactured by Takara; the reagents for genetic engineering used in Example were those manufactured by Takara unless otherwise mentioned), a single-stranded cDNA was synthesized.

Genes (cDNAs) coding for the H chain and the L chain of an antibody have the structure as shown in FIG. 1. Oligonucleotides having the nucleotide sequences of the leader sequence at the 5' end (MHL74, MKL74) and of the J region at the 3' end (MHJ3, MKJ1D7) were prepared, respectively, as primers for amplification of the VH chain and Vκ chain genes. The nucleotide sequence of the primers was as follows:

Primer for amplification of the VH chain gene:

MHL74: AAGCTTGCCGCCACCATGAAATGCAGC TGGGT(T/C)AT (SEQ ID NO: 19 and 20)

MHJ3: GAAGATCTGGATCCACTCACCTGCA-GAGACAGTGA (SEQ ID NO: 21)

Primer for amplification of the Vκ chain gene:

MKL74: CTTAAGCTTGCCGCCACCATGAGTGTGC TCACTCAGGT (SEQ ID NO: 22)

MKJ1D7: CTAGATCTGGATCCACTTACGTTTGATT TCCAGCCT (SEQ ID NO: 23)

Figure 2:
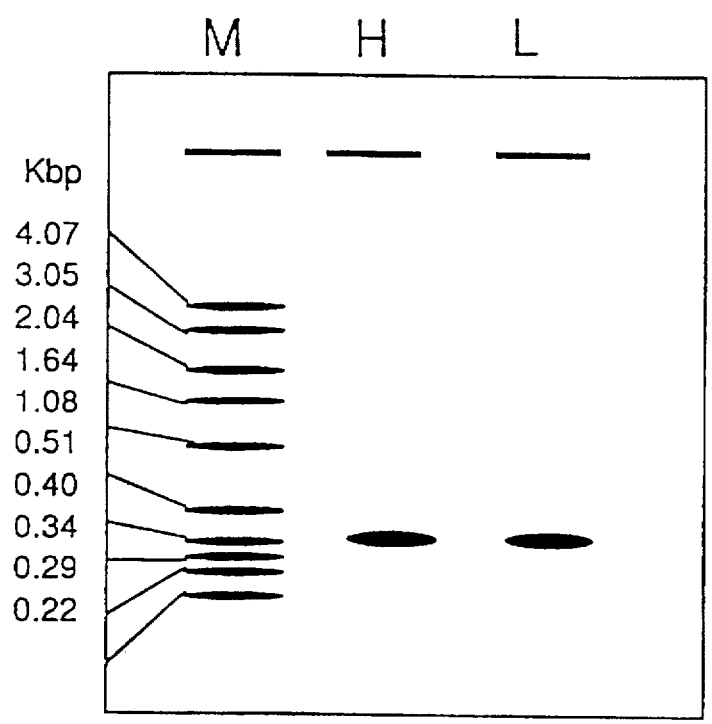
FIG. 2 illustrates the agarose gel electrophoretic analysis of PCR-amplified gene fragments coding for VH and Vκ of the anti-FCV antibody 1D7.

Each 50 pmoles of primers was added to 20 ng of CDNA. Polymerase chain reaction (PCR) was conducted for 30 cycles, each cycle comprising 94° C. for 1 minute, 55° C. for 1 minute and 72° C. for 1 minute, to amplify the genes coding for the variable region (VH, Vκ) flanked by the primers. FIG. 2 shows a pattern of the amplified genes by an agarose electrophoresis analysis. A size of the genes was confirmed to be about 400 bp for the VH gene (H chain) and about 400 bp for the Vκ gene (L chain) and nearly corresponded to that of the expected band.

(3) Determination of the nucleotide sequence of VH and Vκ genes:

The nucleotide sequence of each of the gene fragments amplified in the step (2) was determined by the dideoxy chain termination method. The VH and Vκ gene fragments were cloned into pUC18 and the nucleotide sequence of the gene fragments was determined by the dideoxy chain termination method (Sequenase ver. 2 manufactured by USB).

FIG. 3 shows the nucleotide sequence of the gene coding for VH of the 1D7 antibody and the amino acid sequence coded thereby. This gene consisted of open reading frame (ORF) and retained the amino acid Cys which forms the domain structure, and hence, was confirmed to be an expression-type gene. It was also found that the rearrangement occurred at the JH3 region. Then, a homology of the amino acid sequence coded by this gene was searched based on data base of Gene Bank using GENETYX-CD (manufactured by Software) as a software for reference. As a result, antibodies 1 to 5 belonging to VHIII/J606 family were found to show a high homology (FIG. 5). In FIG. 5, the symbol (*) shows those amino acids having homology to other antibodies and the remaining amino acids are those found only in 1D7. The underlined amino acid sequence is a novel sequence which has hitherto never been reported, and hence, is specific to the 1D7 antibody.

FIG. 4 shows the nucleotide sequence of the gene coding for Vκ of the 1D7 antibody and the amino acid sequence coded thereby. This gene consisted of ORF and retained the amino acid Cys which forms the domain structure, and hence, was confirmed to be an expression-type gene. It was also found that the rearrangement occurred at the Jκ1 region. FIG. 6 shows the results of search for homology. The Vκ of 1D7 showed homology to the Vκ of other antibodies. Especially, the underlined sequence is a novel amino acid sequence which has hitherto never been reported, and hence, is specific to the 1D7 antibody.

That is, the underlined sequences in the VH chain and the Vκ chain are specific to the 1D7 antibody and were estimated to be essential for determination of the antigen-binding activity of the antibody.

Figure 7:
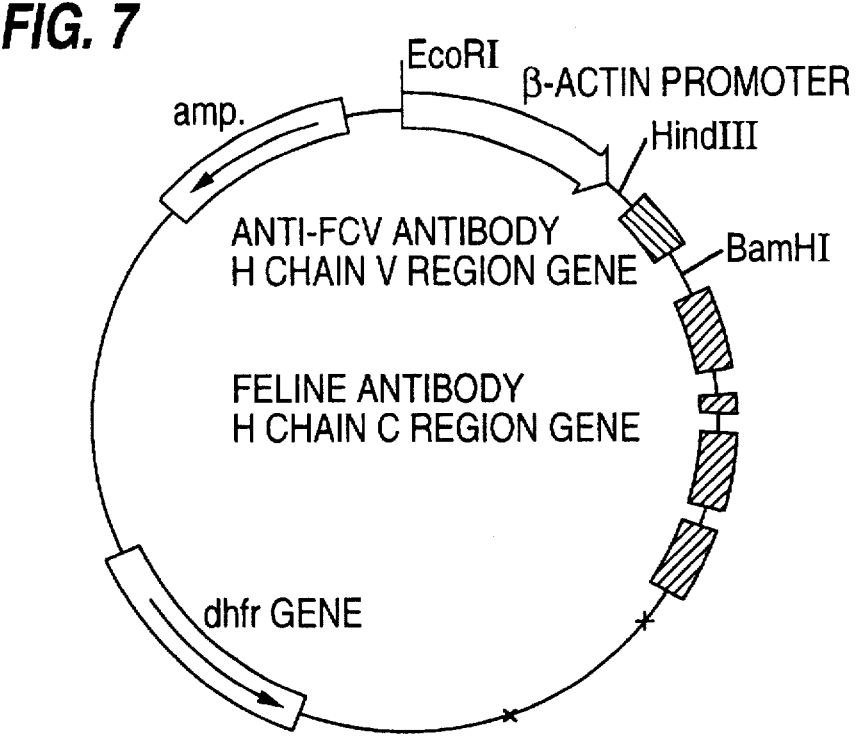
FIG. 7 shows a restriction enzyme map of a vector expressing anti-FCV chimeric antibody H chain.
Figure 8:
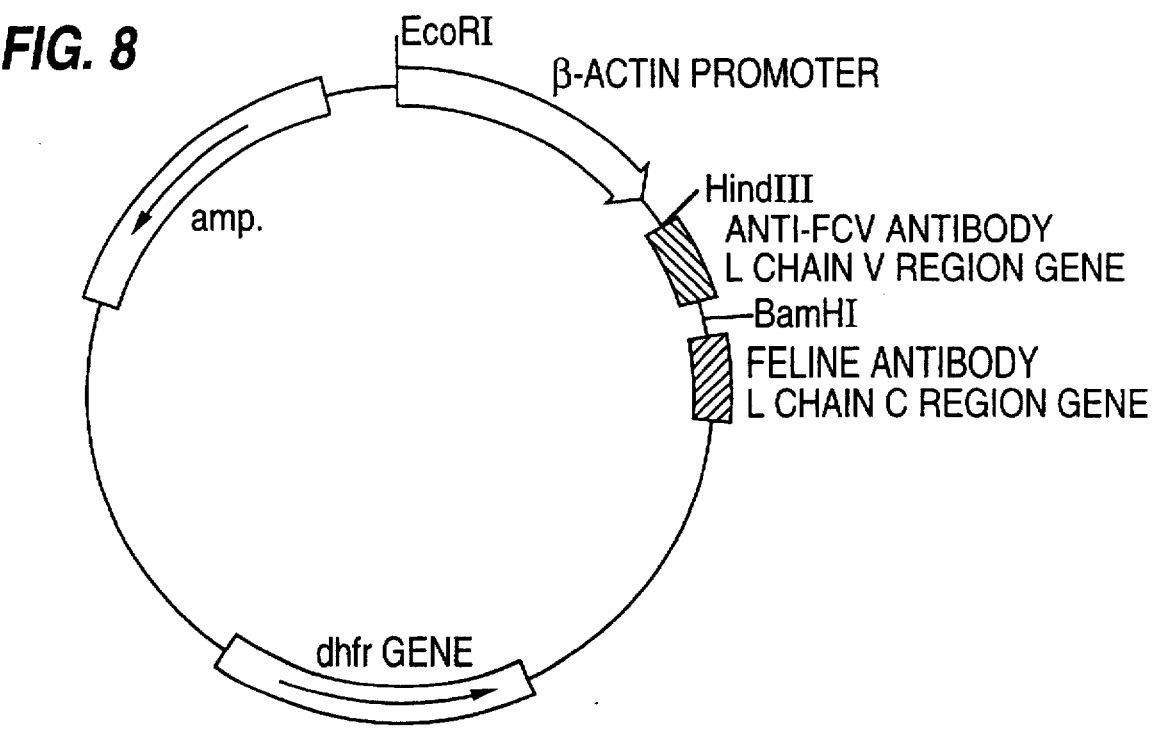
FIG. 8 shows a restriction enzyme map of a vector expressing anti-FCV chimeric antibody L chain.

(4) Preparation of a gene coding for anti-FCV chimeric antibody:

Each of the genes coding for the variable region amplified by PCR was linked to the gene coding for the γ chain constant region (CB25γ; EP 417486A) or the gene coding for the κ chain constant region (CEK; EP 417486A) of feline antibody. A chicken β-actin promoter (Japanese Patent Application No. 309785/1989) was used as an expression promoter and a dhfr gene (Stark, G. R. and Wahl, G. M., Annu. Rev. Biochem., 53, 447, 1984) was used as a selection marker gene. FIGS. 7 and 8 show a restriction enzyme map of the expression vectors for chimeric antibody H chain and L chain, respectively.

(5) Preparation of stable transformant:

Each 10 μg of the genes coding for the chimeric antibody H chain and L(κ) chain shown in FIGS. 7 and 8 was digested with PvuI, and the digested products were cotransfected with $2 \times 10^6$ mouse myeloma cells P3-X63-Ag8-6.5.3. (ATCC CRL 1580) using lipofectin (manufactured by BRL) and then cultured on 5% FCS/RPMI1640 selection culture medium containing $0.25 \times 10^{-7}$M methotrexate (MTX), and thereby the drug-tolerant cells (transformants) were selected.

Cells capable of producing the chimeric antibody were cloned by the limiting dilution method based on feline IgG expressed in the culture supernatant to establish the chimeric antibody-expressing cell F1D7. Properties of the obtained cell F1D7 were analyzed by the following procedures.

Figure 9:
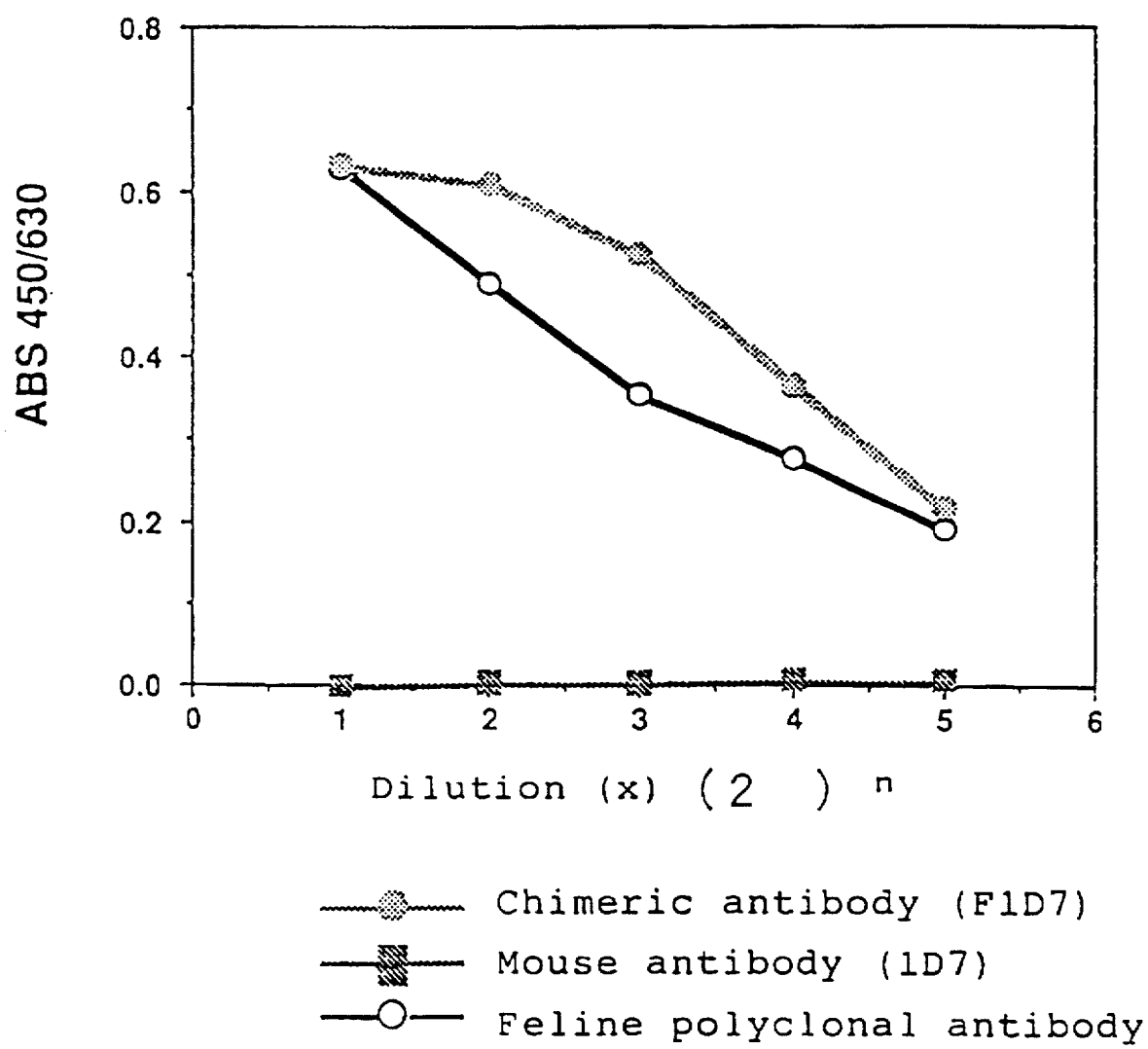
FIG. 9 is a graph showing a reactivity of the chimeric antibody of the present invention with the anti-feline antibody.

(6) Reaction with an anti-feline antibody:

The culture supernatants of F1D7 (chimeric antibody-expressing cells) and of 1D7 (mouse monoclonal antibody-expressing cells) were added to a microtiter plate where an anti-feline antibody (E. Y. LABS. INC) was immobilized and the reaction was conducted at room temperature for 1 hour. After washing the plate, an HRP-anti-feline antibody (E. Y. LABS. INC) was reacted at room temperature for 1 hour. After the plate was washed again, the plate was treated with TMBZ for coloring reaction and an absorbance at 450 nm was measured in order to examine the reactivity with the anti-feline antibody (FIG. 9).

The culture supernatant of F1D7 reacted with the anti-feline antibody depending on a concentration thereof, while the culture supernatant of 1D7 expressing the mouse antibody did not react with the anti-feline antibody. This proved that the chimeric antibody expressed by the F1D7 cells was a feline-type antibody.

(7) Identification of the chimeric antibody by SDS-PAGE:

The chimeric antibody was purified from the culture supernatant with Protein A (manufactured by Bio Rad; MAPS-II). The obtained purified chimeric antibody was subjected to 12.5% SDS-PAGE and compared with a feline IgG sample (polyclonal antibody). The molecular weight was determined by a prestained marker manufactured by Bio-Rad.

Figure 10:
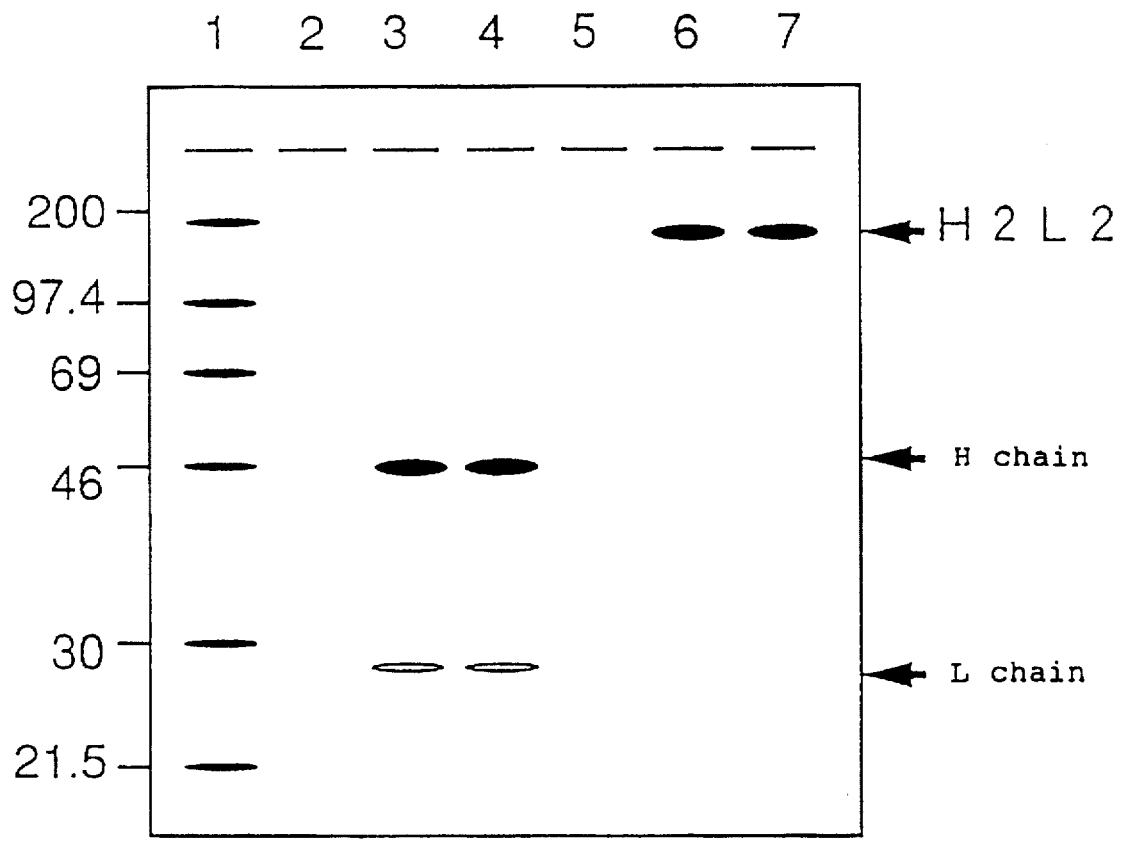
FIG. 10 illustrates the SDS-PAGE analysis of the chimeric antibody of the present invention.

As shown in FIG. 10, the chimeric antibody showed the same size as that of the feline antibody (IgG) sample (lane3/lane4 and lane6/lane7) and the band was detected at about 150,000 under the non-reductive conditions. From these observations, it was found that the chimeric antibody is a dimer of H2L2 and forms the same shape as that of IgG found in the living body of cats.

Figure 11:
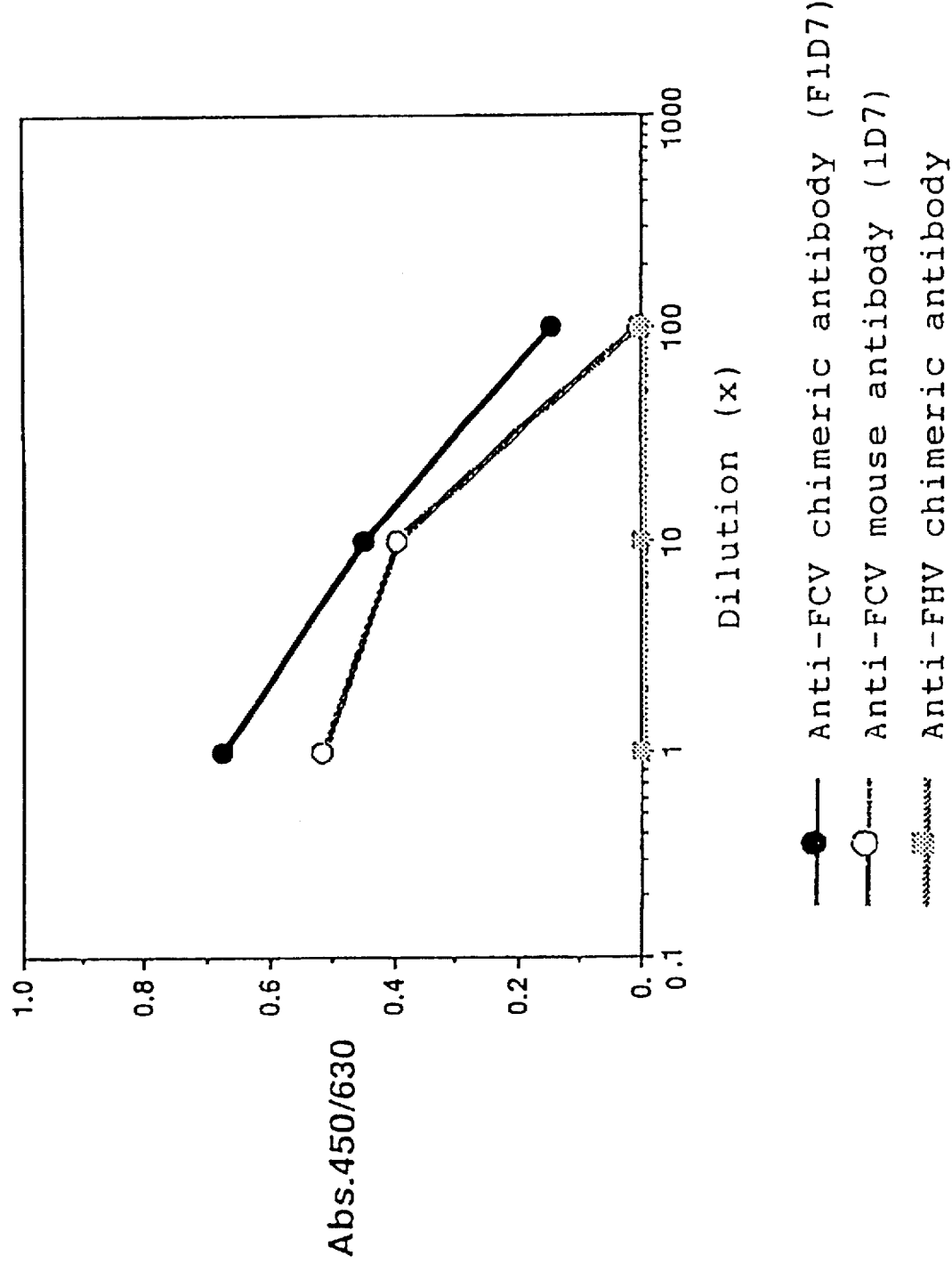
FIG. 11 is a graph showing the binding ability of the chimeric antibody of the present invention to FCV.

(8) Reaction with FCV viral particle:

Then, the antigen-binding activity of the chimeric antibody was examined. The culture supernatants of F1D7 and 1D7 were added to a microtiter plate where FCV-F4 (crude product obtained by precipitation with ammonium sulfate) was immobilized. After washing the plate, an HRP-anti-feline antibody or an HRP-anti-mouse antibody was reacted. Coloring reaction was conducted with TMBZ and the reactivity with the FCV viral particle was examined. The chimeric antibody reacted specifically with the FCV-F4 like the mouse antibody 1D7. However, the recombinant chimeric antibody specific to another virus (antibody comprising the same feline constant region and a different mouse variable region) did not react with the FCV-F4 (FIG. 11).

(9) FCV virus neutralization test:

FCV-neutralizing activity of the chimeric antibody was examined. The culture supernatants of F1D7 and 1D7 were reacted with FCV virus 100TCID$_{50}$ at 4° C. for 6 hours. $0.25 \times 10^5$ CRFK cells were added to the plate and cultured at 37° C. for 2 days. Cytopathic effect (CPE; in this case, cell rounding) was observed and a minimum effective neutralizing concentration was determined.

The results are shown in Table 1. As shown in the table, the chimeric antibody was confirmed to neutralize FCV at 187 ng/ml.

TABLE 1

| Antibody | Minimum effective neutralizing concentration (ng/ml) |
|---|---|
| Chimeric antibody | 186.9 |
| Mouse antibody | 208.2 |

Then, it was examined whether the complement-dependent neutralization activity is enhanced by the binding of F1D7 with complement. Fresh isolated blood of SPF cats (Liberty Laboratory) was centrifuged at a low rate to give serum. The obtained serum was added to Eagle's MEM at a final concentration of 20% with or without inactivation by heating at 56° C. for 30 minutes. F1D7 antibody diluted with this serum mixture was added to a 96-well plate for culture (50 μl/well). FCV-F4 strain was added to the plate at 100TCID$_{50}$/50 μl/well and incubated at 37° C. for 1 hour and therein $0.5 \times 10^6$/ml CRFK cells were inoculated at 100 μl/well. The cells were cultured at 37° C., and after 3 days, the neutralization antibody titer was measured based on CPE. The results are shown in FIG. 12 which depicts a viral neutralization curve under conditions with or without inactivation of complement by heating. As shown in FIG. 12, although F1D7 antibody neutralized FCV-F4 strain under both conditions, it showed neutralization activity at a lower concentration under the non-inactivation condition. This exhibits that the neutralization activity of F1D7 was enhanced under the presence of complement.

When the mouse antibody 1D7 and the felinized antibody F1D7 are compared, 1D7 will show weaker bonding with feline complement in serum since it is a heterogenic antibody derived from mice, while F1D7 will bind feline complement with higher affinity since its constant region is derived from cats. The neutralization activity under the presence of complement was compared between the mouse antibody 1D7 and the felinized antibody F1D7(FIG. 13). Fifty percent inhibitory concentration of F1D7 and 1D7 was 9.572 μg/ml and 1 μg/ml, respectively, and hence, F1D7 had about twice neutralization activity as compared with 1D7.

As mentioned above, F1D7 bound to feline complement and showed more potent neutralization activity than 1D7. Therefore, F1D7 is more advantageous than 1D7 for administration into the cat body since F1D7 contains Fc region derived from cats.

(10) In vivo efficacy test of anti-FCV chimeric antibody:

12 FCV antibody negative SPF cats (age: 4–5 months) were used. All cats were infected with FCV by inoculating FRI-14 strain at $10^7$ TCID$_{50}$ intranasally. The animals were divided into three groups each comprised of four cats, i.e. the first group and second group with intravenous administration of 5 or 10 mg per 1 kg body weight of the feline-type chimeric antibody, respectively, and the third group without administration of the antibody which was used as infection control, and the test animals were observed clinically for 21 days.

Figure 14A:
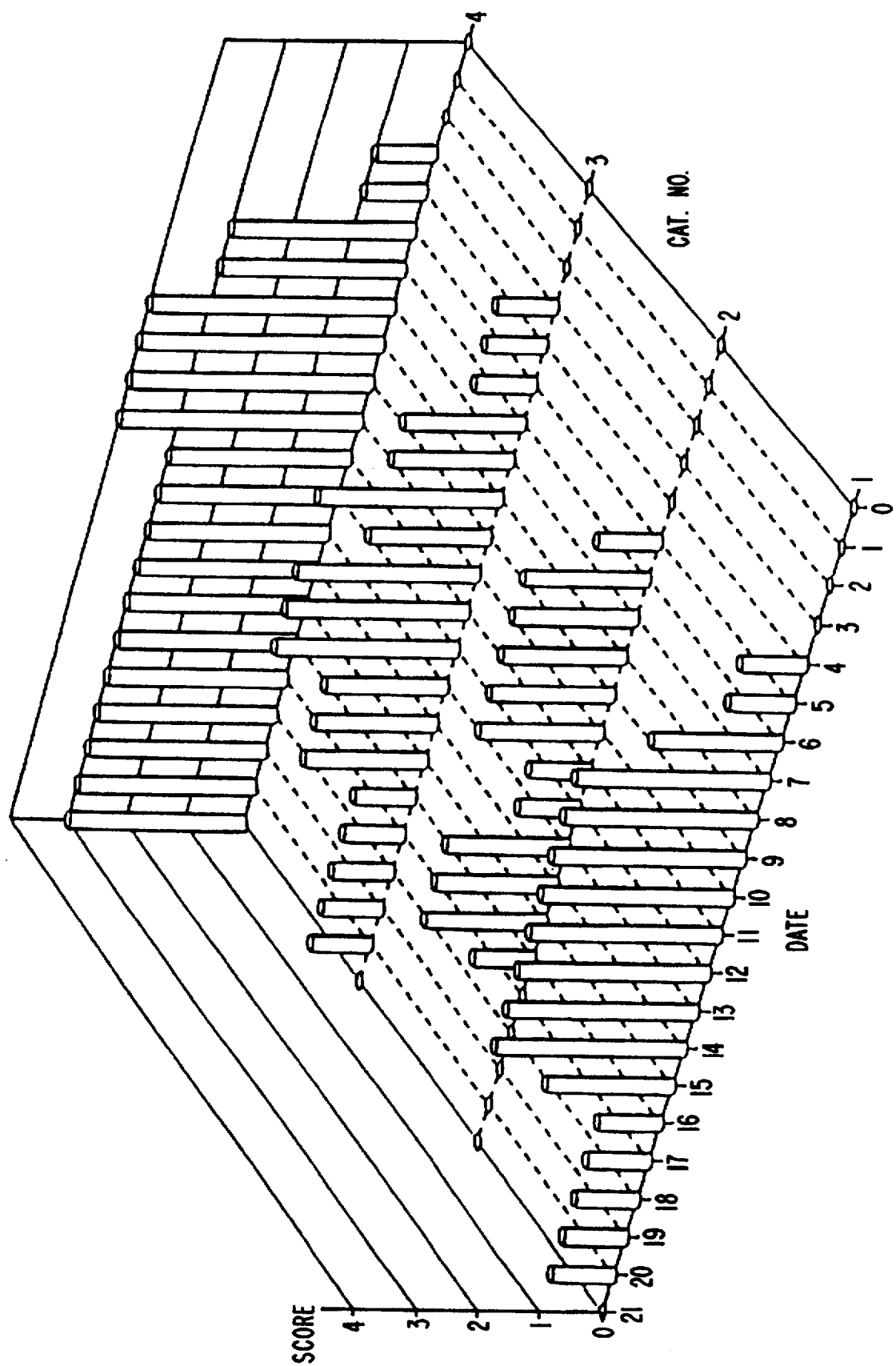
FIG. 14 shows scores of symptoms (stomatitis) observed in the infection control group (a), in the group with F1D7 administration (5 mg/kg)(b) and in the group with F1D7 administration (10 mg/kg).

The infection control group showed symptoms such as decreased food consumption, decreased water consumption, hypersalivation, ophthalmia, etc. as well as fever. On the contrary, the first and second groups with administration of the feline-type chimeric antibody (F1D7) did not show symptoms such as decreased food consumption, decreased water consumption, hypersalivation, ophthalmia, etc. and showed less fever. Specific symptoms of FIC is stomatitis. Therefore, clinical symptoms, mainly stomatitis, of each group were scored and the treating efficacy of the chimeric antibody of the present invention was estimated (FIG. 14). As shown in FIG. 14, heavy stomatitis was observed in the infection control group, but in the groups with the chimeric antibody (F1D7) administration, almost no stomatitis was observed. Wilcoxon Test was conducted between these groups, and as a result, a significant difference with 5% risk was found.

The above results confirmed that the feline-type chimeric antibody (F1D7) of the present invention is effective for treating FCI.

(11) Safety test of feline-type chimeric antibody:

Considering that the antibody of the present invention will be administered repeatedly, the safety test was conducted with various doses of a purified mouse-type antibody and the feline-type antibody of the present invention using cats in the field.

Each of these antibodies was administered to the cats subcutaneously at 1 mg/kg or 5 mg/kg, and three weeks after the administration, 10 mg/kg or 50 mg/kg of each of the antibodies was again administered to the cats intravenously and the clinical state of the cats was observed. As a result, the cats administered with the mouse-type antibody showed typical anaphylactic reactions such as decrease of blood pressure, paleness, prostration, and the like, while the cats administered with the feline-type antibody of the present invention did not show such abnormalities and it was confirmed that the feline-type antibody of the present invention is safe. Table 2 shows the effects of the antibodies on decrease of blood pressure.

TABLE 2

| Antibody type | Dose | Blood pressure before administration (mmHg) | Blood pressure decrease after administration |
|---|---|---|---|
| Mouse-type | low | 86–110 | + |
| | high | 85–113 | ++ |
| Feline-type | low | 89–115 | − |
| | high | 82–116 | − |

(Note)
−: Normal
+: 60 to 80 mmHg
++: less than 60 mmHg

From the above results of the binding experiments and the neutralization test, the chimeric antibody expressed by the F1D7 was confirmed to be a chimeric antibody having a specificity against FCV. This chimeric antibody had the same structure and the antigenicity as those of the original feline antibody found in the living body of cats. This allows for application of the chimeric antibody of the present invention as effective agents for diagnosis, treatment and prevention of FCI without side effects.

What is claimed is:

1. A genetically-engineered recombinant antibody capable of specifically reacting with a feline calicivirus comprising VH and VL regions which have the amino acid sequence from the 20th to the 136th amino acid of SEQ ID NO: 1 and the amino acid sequence from the 21st to the 123rd amino acid of SEQ ID NO: 2, respectively, and H and L constant regions having an amino acid sequence derived from a feline antibody.

2. The antibody of claim 1 wherein an H chain constant region has the amino acid sequence shown in the Sequence Listing as SEQ ID NO: 3 and an L chain constant region has the amino acid sequence shown in the Sequence Listing as SEQ ID NO: 4 or the amino acid sequence shown in the Sequence Listing as SEQ ID NO: 5.

3. A composition for the treatment of feline caliciviral infection, which comprises a genetically-engineered recombinant antibody as set forth in claim 1 or 2 in admixture with a conventional carrier or diluent.

* * * * *

SEQUENCE LISTING ( 1 ) GENERAL INFORMATION:

( i i i ) NUMBER OF SEQUENCES: 23

( 2 ) INFORMATION FOR SEQ ID NO:1:

( i ) SEQUENCE CHARACTERISTICS:
( A ) LENGTH: 409 base pairs
( B ) TYPE: nucleic acid
( C ) STRANDEDNESS: double
( D ) TOPOLOGY: linear ( i i ) MOLECULE TYPE: cDNA to mRNA ( i x ) FEATURE:
( A ) NAME/KEY: CDS
( B ) LOCATION: 1..408

( x i ) SEQUENCE DESCRIPTION: SEQ ID NO:1:

| ATG | AAA | TGC | AGC | TGG | GTT | ATC | TTC | TTC | CTG | ATG | GCA | GTG | GTT | ACA | GGG | 4 8 |
|---|---|---|---|---|---|---|---|---|---|---|---|---|---|---|---|---|
| Met | Lys | Cys | Ser | Trp | Val | Ile | Phe | Phe | Leu | Met | Ala | Val | Val | Thr | Gly | |

-continued

|   | 1 |   |   |   | 5 |   |   |   |   | 10 |   |   |   |   | 15 |   |   |
|---|---|---|---|---|---|---|---|---|---|----|---|---|---|---|----|---|---|

```
GTC  AAT  TCA  GAG  GTT  CAG  CTG  CAG  CAG  TCT  GGG  GCA  GAA  CTT  GTG  AAG        96
Val  Asn  Ser  Glu  Val  Gln  Leu  Gln  Gln  Ser  Gly  Ala  Glu  Leu  Val  Lys
               20                        25                       30

CCA  GGG  GCC  TCA  GTC  AGG  TTG  TCC  TGT  ACA  GCT  TCT  GGC  TTC  AAC  ATT       144
Pro  Gly  Ala  Ser  Val  Arg  Leu  Ser  Cys  Thr  Ala  Ser  Gly  Phe  Asn  Ile
               35                        40                       45

AAA  GAC  ACC  TAT  ATG  CAC  TGG  GTG  AAA  CAG  AGG  CCT  GAA  CAG  GGC  CTG       192
Lys  Asp  Thr  Tyr  Met  His  Trp  Val  Lys  Gln  Arg  Pro  Glu  Gln  Gly  Leu
               50                        55                       60

GAG  TGG  ATT  GGA  AGG  ATT  GAT  CCT  GCA  AAT  GGT  AAT  ACT  AAA  TAT  GAC       240
Glu  Trp  Ile  Gly  Arg  Ile  Asp  Pro  Ala  Asn  Gly  Asn  Thr  Lys  Tyr  Asp
65                        70                        75                       80

CCG  AGG  TTC  CAG  GGC  AAG  GCC  ACT  ATA  ACA  GCA  GAC  ACA  TCC  TTC  AAC       288
Pro  Arg  Phe  Gln  Gly  Lys  Ala  Thr  Ile  Thr  Ala  Asp  Thr  Ser  Phe  Asn
               85                        90                       95

ACA  GCC  TAC  CTG  CAA  GTC  AAC  AGC  CTG  ACA  TCT  GAG  GAC  ACT  GCC  GTC       336
Thr  Ala  Tyr  Leu  Gln  Val  Asn  Ser  Leu  Thr  Ser  Glu  Asp  Thr  Ala  Val
               100                       105                      110

TAT  TAC  TGT  GCT  AGC  GGG  GGT  AAT  GCC  TGG  CTT  GCT  TAC  TGG  GGC  CAA       384
Tyr  Tyr  Cys  Ala  Ser  Gly  Gly  Asn  Ala  Trp  Leu  Ala  Tyr  Trp  Gly  Gln
               115                       120                      125

GGG  ACT  CTG  GTC  ACT  GTC  TCT  GCA  G                                          409
  Gly  Thr  Leu  Val  Thr  Val  Ser  Ala
       130                 135
```

( 2 ) INFORMATION FOR SEQ ID NO:2:

( i ) SEQUENCE CHARACTERISTICS:
        ( A ) LENGTH: 136 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Lys  Cys  Ser  Trp  Val  Ile  Phe  Phe  Leu  Met  Ala  Val  Val  Thr  Gly
1                   5                        10                       15

Val  Asn  Ser  Glu  Val  Gln  Leu  Gln  Gln  Ser  Gly  Ala  Glu  Leu  Val  Lys
               20                        25                       30

Pro  Gly  Ala  Ser  Val  Arg  Leu  Ser  Cys  Thr  Ala  Ser  Gly  Phe  Asn  Ile
               35                        40                       45

Lys  Asp  Thr  Tyr  Met  His  Trp  Val  Lys  Gln  Arg  Pro  Glu  Gln  Gly  Leu
               50                        55                       60

Glu  Trp  Ile  Gly  Arg  Ile  Asp  Pro  Ala  Asn  Gly  Asn  Thr  Lys  Tyr  Asp
65                        70                        75                       80

Pro  Arg  Phe  Gln  Gly  Lys  Ala  Thr  Ile  Thr  Ala  Asp  Thr  Ser  Phe  Asn
               85                        90                       95

Thr  Ala  Tyr  Leu  Gln  Val  Asn  Ser  Leu  Thr  Ser  Glu  Asp  Thr  Ala  Val
               100                       105                      110

Tyr  Tyr  Cys  Ala  Ser  Gly  Gly  Asn  Ala  Trp  Leu  Ala  Tyr  Trp  Gly  Gln
               115                       120                      125

Gly  Thr  Leu  Val  Thr  Val  Ser  Ala
     130                 135
```

( 2 ) INFORMATION FOR SEQ ID NO:3:

( i ) SEQUENCE CHARACTERISTICS:
        ( A ) LENGTH: 385 base pairs
        ( B ) TYPE: nucleic acid
        ( C ) STRANDEDNESS: double ( D ) TOPOLOGY: linear ( i i ) MOLECULE TYPE: cDNA to mRNA ( i x ) FEATURE:
    ( A ) NAME/KEY: CDS
    ( B ) LOCATION: 1..385

( x i ) SEQUENCE DESCRIPTION: SEQ ID NO:3:

```
ATG AGT GTG CTC ACC CAG GTG CTG GCG TGG CTG CTG CTG TGG CTT ACA        48
Met Ser Val Leu Thr Gln Val Leu Ala Trp Leu Leu Leu Trp Leu Thr
 1               5                  10                  15

GGT GCC AGA TGT GAC ATC CAG ATG ACT CAG TCT CCA GCC TCC CTA TCT        96
Gly Ala Arg Cys Asp Ile Gln Met Thr Gln Ser Pro Ala Ser Leu Ser
                20                  25                  30

GCA TCT GTG GGA GAA ACT GTC ACC ATC ACA TGT CGA GCA AGT GGG AAT       144
Ala Ser Val Gly Glu Thr Val Thr Ile Thr Cys Arg Ala Ser Gly Asn
         35                  40                  45

ATT CAC AAT TAT TTA GCA TGG TAT CAG AAG AAA CAG GGA AAA TCT CCT       192
Ile His Asn Tyr Leu Ala Trp Tyr Gln Lys Lys Gln Gly Lys Ser Pro
     50                  55                  60

CAG CTC CTG GTC TAT AGT GCA GAA AGT TTA GCA GTT GGT GTG CCA TCA       240
Gln Leu Leu Val Tyr Ser Ala Glu Ser Leu Ala Val Gly Val Pro Ser
 65                  70                  75                  80

AGG TTC AGT GGC AGT GGA TCA GAA ACA CAC TAT TTT CTC AAG ATC GAC       288
Arg Phe Ser Gly Ser Gly Ser Glu Thr His Tyr Phe Leu Lys Ile Asp
                 85                  90                  95

AGC CTG CAG CCT GAA GAT TTT GGG AGT TAT TAC TGT CAA AAT TTT TGG       336
Ser Leu Gln Pro Glu Asp Phe Gly Ser Tyr Tyr Cys Gln Asn Phe Trp
            100                 105                 110

ACT ACT CCG TGG ACG TTC GGT GGA GGC ACC AGG TTG GAA TTC AAA CGG G     385
Thr Thr Pro Trp Thr Phe Gly Gly Gly Thr Arg Leu Glu Phe Lys Arg
        115                 120                 125
```

( 2 ) INFORMATION FOR SEQ ID NO:4:

( i ) SEQUENCE CHARACTERISTICS:
        ( A ) LENGTH: 128 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met Ser Val Leu Thr Gln Val Leu Ala Trp Leu Leu Leu Trp Leu Thr
 1               5                  10                  15

Gly Ala Arg Cys Asp Ile Gln Met Thr Gln Ser Pro Ala Ser Leu Ser
                20                  25                  30

Ala Ser Val Gly Glu Thr Val Thr Ile Thr Cys Arg Ala Ser Gly Asn
         35                  40                  45

Ile His Asn Tyr Leu Ala Trp Tyr Gln Lys Lys Gln Gly Lys Ser Pro
     50                  55                  60

Gln Leu Leu Val Tyr Ser Ala Glu Ser Leu Ala Val Gly Val Pro Ser
 65                  70                  75                  80

Arg Phe Ser Gly Ser Gly Ser Glu Thr His Tyr Phe Leu Lys Ile Asp
                 85                  90                  95

Ser Leu Gln Pro Glu Asp Phe Gly Ser Tyr Tyr Cys Gln Asn Phe Trp
            100                 105                 110

Thr Thr Pro Trp Thr Phe Gly Gly Gly Thr Arg Leu Glu Phe Lys Arg
        115                 120                 125
```

( 2 ) INFORMATION FOR SEQ ID NO:5:

(i) SEQUENCE CHARACTERISTICS:
(A) LENGTH: 1005 base pairs
(B) TYPE: nucleic acid
(C) STRANDEDNESS: double
(D) TOPOLOGY: linear (ii) MOLECULE TYPE: cDNA to mRNA (ix) FEATURE:
(A) NAME/KEY: CDS
(B) LOCATION: 1..999

(xi) SEQUENCE DESCRIPTION: SEQ ID NO:5:

| ACC | ACG | GCC | CCA | TCG | GTG | TTC | CCA | CTG | GCC | CCC | AGC | TGC | GGG | ACC | ACA | 48 |
| Thr | Thr | Ala | Pro | Ser | Val | Phe | Pro | Leu | Ala | Pro | Ser | Cys | Gly | Thr | Thr | |
| 1 | | | | 5 | | | | | 10 | | | | | 15 | | |

| TCT | GGC | GCC | ACC | GTG | GCC | CTG | GCC | TGC | CTG | GTG | TTA | GGC | TAC | TTC | CCT | 96 |
| Ser | Gly | Ala | Thr | Val | Ala | Leu | Ala | Cys | Leu | Val | Leu | Gly | Tyr | Phe | Pro | |
| | | | 20 | | | | | 25 | | | | | 30 | | | |

| GAG | CCG | GTG | ACC | GTG | TCC | TGG | AAC | TCC | GGC | GCC | CTG | ACC | AGC | GGT | GTG | 144 |
| Glu | Pro | Val | Thr | Val | Ser | Trp | Asn | Ser | Gly | Ala | Leu | Thr | Ser | Gly | Val | |
| | | 35 | | | | | 40 | | | | | 45 | | | | |

| CAC | ACC | TTC | CCG | GCC | GTC | CTG | CAG | GCC | TCG | GGG | CTG | TAC | TCT | CTC | AGC | 192 |
| His | Thr | Phe | Pro | Ala | Val | Leu | Gln | Ala | Ser | Gly | Leu | Tyr | Ser | Leu | Ser | |
| | 50 | | | | | 55 | | | | | 60 | | | | | |

| AGC | ATG | GTG | ACA | GTG | CCC | TCC | AGC | AGG | TGG | CTC | AGT | GAC | ACC | TTC | ACC | 240 |
| Ser | Met | Val | Thr | Val | Pro | Ser | Ser | Arg | Trp | Leu | Ser | Asp | Thr | Phe | Thr | |
| 65 | | | | | 70 | | | | | 75 | | | | | 80 | |

| TGC | AAC | GTG | GCC | CAC | CCG | CCC | AGC | AAC | ACC | AAG | GTG | GAC | AAG | ACC | GTG | 288 |
| Cys | Asn | Val | Ala | His | Pro | Pro | Ser | Asn | Thr | Lys | Val | Asp | Lys | Thr | Val | |
| | | | | 85 | | | | | 90 | | | | | 95 | | |

| CGC | AAA | ACA | GAC | CAC | CCA | CCG | GGA | CCC | AAA | CCC | TGC | GAC | TGT | CCC | AAA | 336 |
| Arg | Lys | Thr | Asp | His | Pro | Pro | Gly | Pro | Lys | Pro | Cys | Asp | Cys | Pro | Lys | |
| | | | 100 | | | | | 105 | | | | | 110 | | | |

| TGC | CCA | CCC | CCT | GAG | ATG | CTT | GGA | GGA | CCG | TCC | ATC | TTC | ATC | TTC | CCC | 384 |
| Cys | Pro | Pro | Pro | Glu | Met | Leu | Gly | Gly | Pro | Ser | Ile | Phe | Ile | Phe | Pro | |
| | | 115 | | | | | 120 | | | | | 125 | | | | |

| CCA | AAA | CCC | AAG | GAC | ACC | CTC | TCG | ATT | TCC | CGG | ACG | CCC | GAG | GTC | ACA | 432 |
| Pro | Lys | Pro | Lys | Asp | Thr | Leu | Ser | Ile | Ser | Arg | Thr | Pro | Glu | Val | Thr | |
| | 130 | | | | | 135 | | | | | 140 | | | | | |

| TGC | TTG | GTG | GTG | GAC | TTG | GGC | CCA | GAT | GAC | TCC | GAT | GTC | CAG | ATC | ACA | 480 |
| Cys | Leu | Val | Val | Asp | Leu | Gly | Pro | Asp | Asp | Ser | Asp | Val | Gln | Ile | Thr | |
| 145 | | | | | 150 | | | | | 155 | | | | | 160 | |

| TGG | TTT | GTG | GAT | AAC | ACC | CAG | GTG | TAC | ACA | GCC | AAG | ACG | AGT | CCG | CGT | 528 |
| Trp | Phe | Val | Asp | Asn | Thr | Gln | Val | Tyr | Thr | Ala | Lys | Thr | Ser | Pro | Arg | |
| | | | | 165 | | | | | 170 | | | | | 175 | | |

| GAG | GAG | CAG | TTC | AAC | AGC | ACC | TAC | CGT | GTG | GTC | AGT | GTC | CTC | CCC | ATC | 576 |
| Glu | Glu | Gln | Phe | Asn | Ser | Thr | Tyr | Arg | Val | Val | Ser | Val | Leu | Pro | Ile | |
| | | | 180 | | | | | 185 | | | | | 190 | | | |

| CTA | CAC | CAG | GAC | TGG | CTC | AAG | GGG | AAG | GAG | TTC | AAG | TGC | AAG | GTC | AAC | 624 |
| Leu | His | Gln | Asp | Trp | Leu | Lys | Gly | Lys | Glu | Phe | Lys | Cys | Lys | Val | Asn | |
| | | 195 | | | | | 200 | | | | | 205 | | | | |

| AGC | AAA | TCC | CTC | CCC | TCC | CCC | ATC | GAG | AGG | ACC | ATC | TCC | AAG | GCC | AAA | 672 |
| Ser | Lys | Ser | Leu | Pro | Ser | Pro | Ile | Glu | Arg | Thr | Ile | Ser | Lys | Ala | Lys | |
| | 210 | | | | | 215 | | | | | 220 | | | | | |

| GGA | CAG | CCC | CAC | GAG | CCC | CAG | GTG | TAC | GTC | CTG | CCT | CCA | GCC | CAG | GAG | 720 |
| Gly | Gln | Pro | His | Glu | Pro | Gln | Val | Tyr | Val | Leu | Pro | Pro | Ala | Gln | Glu | |
| 225 | | | | | 230 | | | | | 235 | | | | | 240 | |

| GAG | CTC | AGC | AGG | AAC | AAA | GTC | AGT | GTG | ACC | TGC | CTG | ATC | AAA | AGC | TTC | 768 |
| Glu | Leu | Ser | Arg | Asn | Lys | Val | Ser | Val | Thr | Cys | Leu | Ile | Lys | Ser | Phe | |
| | | | | 245 | | | | | 250 | | | | | 255 | | |

| CAC | CCG | CCT | GAC | ATT | GCC | GTC | GAG | TGG | GAG | ATC | ACC | GGA | CAG | CCG | GAG | 816 |

|   |   |   |   |   |   |   |   |   |   |   |   |   |   |   |   |   |
|---|---|---|---|---|---|---|---|---|---|---|---|---|---|---|---|---|
| His | Pro | Pro | Asp<br>260 | Ile | Ala | Val | Glu | Trp<br>265 | Glu | Ile | Thr | Gly | Gln<br>270 | Pro | Glu | |
| CCA | GAG | AAC | AAC | TAC | CGG | ACG | ACC | CCG | CCC | CAG | CTG | GAC | AGC | GAC | GGG | 864 |
| Pro | Glu | Asn<br>275 | Asn | Tyr | Arg | Thr | Thr<br>280 | Pro | Pro | Gln | Leu | Asp<br>285 | Ser | Asp | Gly | |
| ACC | TAC | TTC | GTG | TAC | AGC | AAG | CTC | TCG | GTG | GAC | AGG | TCC | CAC | TGG | CAG | 912 |
| Thr | Tyr<br>290 | Phe | Val | Tyr | Ser | Lys<br>295 | Leu | Ser | Val | Asp | Arg<br>300 | Ser | His | Trp | Gln | |
| AGG | GGA | AAC | ACC | TAC | ACC | TGC | TCG | GTG | TCA | CAC | GAA | GCT | CTG | CAC | AGC | 960 |
| Arg<br>305 | Gly | Asn | Thr | Tyr | Thr<br>310 | Cys | Ser | Val | Ser | His<br>315 | Glu | Ala | Leu | His | Ser<br>320 | |
| CAC | CAC | ACA | CAG | AAA | TCC | CTC | ACC | CAG | TCT | CCG | GGT | AAA | TGAGCA | | | 1005 |
| His | His | Thr | Gln | Lys<br>325 | Ser | Leu | Thr | Gln | Ser<br>330 | Pro | Gly | Lys | | | | |

( 2 ) INFORMATION FOR SEQ ID NO:6:

( i ) SEQUENCE CHARACTERISTICS:
        ( A ) LENGTH: 333 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

|   |   |   |   |   |   |   |   |   |   |   |   |   |   |   |
|---|---|---|---|---|---|---|---|---|---|---|---|---|---|---|
| Thr<br>1 | Thr | Ala | Pro | Ser<br>5 | Val | Phe | Pro | Leu | Ala<br>10 | Pro | Ser | Cys | Gly | Thr<br>15 | Thr |
| Ser | Gly | Ala | Thr<br>20 | Val | Ala | Leu | Ala | Cys<br>25 | Leu | Val | Leu | Gly | Tyr<br>30 | Phe | Pro |
| Glu | Pro | Val<br>35 | Thr | Val | Ser | Trp | Asn<br>40 | Ser | Gly | Ala | Leu | Thr<br>45 | Ser | Gly | Val |
| His | Thr<br>50 | Phe | Pro | Ala | Val | Leu<br>55 | Gln | Ala | Ser | Gly | Leu<br>60 | Tyr | Ser | Leu | Ser |
| Ser<br>65 | Met | Val | Thr | Val | Pro<br>70 | Ser | Ser | Arg | Trp | Leu<br>75 | Ser | Asp | Thr | Phe | Thr<br>80 |
| Cys | Asn | Val | Ala | His<br>85 | Pro | Pro | Ser | Asn | Thr<br>90 | Lys | Val | Asp | Lys | Thr<br>95 | Val |
| Arg | Lys | Thr | Asp<br>100 | His | Pro | Pro | Gly | Pro<br>105 | Lys | Pro | Cys | Asp | Cys<br>110 | Pro | Lys |
| Cys | Pro | Pro<br>115 | Pro | Glu | Met | Leu | Gly<br>120 | Gly | Pro | Ser | Ile | Phe<br>125 | Ile | Phe | Pro |
| Pro | Lys<br>130 | Pro | Lys | Asp | Thr | Leu<br>135 | Ser | Ile | Ser | Arg | Thr<br>140 | Pro | Glu | Val | Thr |
| Cys<br>145 | Leu | Val | Val | Asp | Leu<br>150 | Gly | Pro | Asp | Asp | Ser<br>155 | Asp | Val | Gln | Ile | Thr<br>160 |
| Trp | Phe | Val | Asp | Asn<br>165 | Thr | Gln | Val | Tyr | Thr<br>170 | Ala | Lys | Thr | Ser | Pro<br>175 | Arg |
| Glu | Glu | Gln | Phe<br>180 | Asn | Ser | Thr | Tyr | Arg<br>185 | Val | Val | Ser | Val | Leu<br>190 | Pro | Ile |
| Leu | His | Gln<br>195 | Asp | Trp | Leu | Lys | Gly<br>200 | Lys | Glu | Phe | Lys | Cys<br>205 | Lys | Val | Asn |
| Ser | Lys<br>210 | Ser | Leu | Pro | Ser | Pro<br>215 | Ile | Glu | Arg | Thr | Ile<br>220 | Ser | Lys | Ala | Lys |
| Gly<br>225 | Gln | Pro | His | Glu | Pro<br>230 | Gln | Val | Tyr | Val | Leu<br>235 | Pro | Pro | Ala | Gln | Glu<br>240 |
| Glu | Leu | Ser | Arg | Asn<br>245 | Lys | Val | Ser | Val | Thr<br>250 | Cys | Leu | Ile | Lys | Ser<br>255 | Phe |
| His | Pro | Pro | Asp | Ile | Ala | Val | Glu | Trp | Glu | Ile | Thr | Gly | Gln | Pro | Glu |

|  | 260 |  |  |  |  | 265 |  |  |  |  | 270 |  |  |  |
|---|---|---|---|---|---|---|---|---|---|---|---|---|---|---|
| Pro | Glu | Asn<br>275 | Asn | Tyr | Arg | Thr | Thr<br>280 | Pro | Pro | Gln | Leu | Asp<br>285 | Ser | Asp | Gly |
| Thr | Tyr<br>290 | Phe | Val | Tyr | Ser<br>295 | Lys | Leu | Ser | Val | Asp<br>300 | Arg | Ser | His | Trp | Gln |
| Arg<br>305 | Gly | Asn | Thr | Tyr | Thr<br>310 | Cys | Ser | Val | Ser | His<br>315 | Glu | Ala | Leu | His | Ser<br>320 |
| His | His | Thr | Gln | Lys<br>325 | Ser | Leu | Thr | Gln | Ser<br>330 | Pro | Gly | Lys |  |  |  |

( 2 ) INFORMATION FOR SEQ ID NO:7:

( i ) SEQUENCE CHARACTERISTICS:
        ( A ) LENGTH: 337 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 1..327

( x i ) SEQUENCE DESCRIPTION: SEQ ID NO:7:

| AGT | GAT | GCT | CAG | CCA | TCT | GTC | TTT | CTC | TTC | CAA | CCA | TCT | CTG | GAC | GAG | 48 |
|---|---|---|---|---|---|---|---|---|---|---|---|---|---|---|---|---|
| Ser<br>1 | Asp | Ala | Gln | Pro<br>5 | Ser | Val | Phe | Leu | Phe<br>10 | Gln | Pro | Ser | Leu | Asp<br>15 | Glu |  |
| TTA | CAT | ACA | GGA | AGT | GCC | TCT | ATC | GTG | TGC | ATA | TTG | AAT | GAC | TTC | TAC | 96 |
| Leu | His | Thr | Gly<br>20 | Ser | Ala | Ser | Ile | Val<br>25 | Cys | Ile | Leu | Asn | Asp<br>30 | Phe | Tyr |  |
| CCC | AAA | GAG | GTC | AAT | GTC | AAG | TGG | AAA | GTG | GAT | GGC | GTA | GTC | CAA | ACA | 144 |
| Pro | Lys | Glu<br>35 | Val | Asn | Val | Lys | Trp<br>40 | Lys | Val | Asp | Gly | Val<br>45 | Val | Gln | Thr |  |
| AAG | GCA | TCC | AAG | GAG | AGC | ACC | ACA | GAG | CAG | AAC | AGC | AAG | GAC | AGC | ACC | 192 |
| Lys | Ala<br>50 | Ser | Lys | Glu | Ser<br>55 | Thr | Thr | Glu | Gln | Asn<br>60 | Ser | Lys | Asp | Ser | Thr |  |
| TAC | AGC | CTC | AGC | AGC | ACC | CTG | ACG | ATG | TCC | AGG | ACG | GAG | TAC | CAA | AGT | 240 |
| Tyr<br>65 | Ser | Leu | Ser | Ser | Thr<br>70 | Leu | Thr | Met | Ser | Arg<br>75 | Thr | Glu | Tyr | Gln | Ser<br>80 |  |
| CAT | GAA | AAG | TTC | TCC | TGC | GAG | GTC | ACT | CAC | AAG | AGC | CTG | GCC | TCC | ACC | 288 |
| His | Glu | Lys | Phe | Ser<br>85 | Cys | Glu | Val | Thr | His<br>90 | Lys | Ser | Leu | Ala | Ser<br>95 | Thr |  |
| CTC | GTC | AAG | AGC | TTC | AAC | AGG | AGC | GAG | TGT | CAG | AGA | GAG | TAGCCTAGCA |  |  | 337 |
| Leu | Val | Lys | Ser<br>100 | Phe | Asn | Arg | Ser | Glu<br>105 | Cys | Gln | Arg | Glu |  |  |  |  |

( 2 ) INFORMATION FOR SEQ ID NO:8:

( i ) SEQUENCE CHARACTERISTICS:
        ( A ) LENGTH: 109 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

| Ser<br>1 | Asp | Ala | Gln | Pro<br>5 | Ser | Val | Phe | Leu | Phe<br>10 | Gln | Pro | Ser | Leu | Asp<br>15 | Glu |
|---|---|---|---|---|---|---|---|---|---|---|---|---|---|---|---|
| Leu | His | Thr | Gly<br>20 | Ser | Ala | Ser | Ile | Val<br>25 | Cys | Ile | Leu | Asn | Asp<br>30 | Phe | Tyr |
| Pro | Lys | Glu<br>35 | Val | Asn | Val | Lys | Trp<br>40 | Lys | Val | Asp | Gly | Val<br>45 | Val | Gln | Thr |

Lys Ala Ser Lys Glu Ser Thr Thr Glu Gln Asn Ser Lys Asp Ser Thr
     50                  55                  60

Tyr Ser Leu Ser Ser Thr Leu Thr Met Ser Arg Thr Glu Tyr Gln Ser
65                  70                  75                  80

His Glu Lys Phe Ser Cys Glu Val Thr His Lys Ser Leu Ala Ser Thr
                85                  90                  95

Leu Val Lys Ser Phe Asn Arg Ser Glu Cys Gln Arg Glu
            100                 105

( 2 ) INFORMATION FOR SEQ ID NO:9:

( i ) SEQUENCE CHARACTERISTICS:
        ( A ) LENGTH: 318 base pairs
        ( B ) TYPE: nucleic acid
        ( C ) STRANDEDNESS: double
        ( D ) TOPOLOGY: linear ( i i ) MOLECULE TYPE: cDNA to mRNA ( i x ) FEATURE:
        ( A ) NAME/KEY: CDS
        ( B ) LOCATION: 1..315

( x i ) SEQUENCE DESCRIPTION: SEQ ID NO:9:

CAG CCC AAG TCG GCC CCC TCG GTC ACA CTC TTC CCA CCC TCC AGT GAG    48
Gln Pro Lys Ser Ala Pro Ser Val Thr Leu Phe Pro Pro Ser Ser Glu
 1               5                  10                  15

GAG CTC AGC GCA AAC AAG GCC ACC CTG GTG TGT CTC GTC AGT GAC TTC    96
Glu Leu Ser Ala Asn Lys Ala Thr Leu Val Cys Leu Val Ser Asp Phe
             20                  25                  30

TAC CCC AGC GGC TTG ACG GTG GCC TGG AAG GAA GAT GGC ACC CCC ATC   144
Tyr Pro Ser Gly Leu Thr Val Ala Trp Lys Glu Asp Gly Thr Pro Ile
         35                  40                  45

ACC AAG GGC GTG GAG ACC ACC AAG CCC TCC AGA CAG AGC AAC AAC AAG   192
Thr Lys Gly Val Glu Thr Thr Lys Pro Ser Arg Gln Ser Asn Asn Lys
     50                  55                  60

TAC GCG GCC AGC AGC TAC CTG AGC CTG TCA CCG AAC GAG TGG AAA TCT   240
Tyr Ala Ala Ser Ser Tyr Leu Ser Leu Ser Pro Asn Glu Trp Lys Ser
65                  70                  75                  80

CAC AGC AGA TAC ACC TGC CAG GTC ACG CAC GAG GGG AGC ACT GTG GAG   288
His Ser Arg Tyr Thr Cys Gln Val Thr His Glu Gly Ser Thr Val Glu
                85                  90                  95

AAG AGT GTG GTC CCT GCA GAG TGC CCT TAG                            318
Lys Ser Val Val Pro Ala Glu Cys Pro
            100                 105

( 2 ) INFORMATION FOR SEQ ID NO:10:

( i ) SEQUENCE CHARACTERISTICS:
        ( A ) LENGTH: 105 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

Gln Pro Lys Ser Ala Pro Ser Val Thr Leu Phe Pro Pro Ser Ser Glu
 1               5                  10                  15

Glu Leu Ser Ala Asn Lys Ala Thr Leu Val Cys Leu Val Ser Asp Phe
             20                  25                  30

Tyr Pro Ser Gly Leu Thr Val Ala Trp Lys Glu Asp Gly Thr Pro Ile
         35                  40                  45

Thr Lys Gly Val Glu Thr Thr Lys Pro Ser Arg Gln Ser Asn Asn Lys
     50                  55                  60

Tyr Ala Ala Ser Ser Tyr Leu Ser Leu Ser Pro Asn Glu Trp Lys Ser
65                  70                  75                  80

His Ser Arg Tyr Thr Cys Gln Val Thr His Glu Gly Ser Thr Val Glu
                85                  90                  95

Lys Ser Val Val Pro Ala Glu Cys Pro
            100                 105

( 2 ) INFORMATION FOR SEQ ID NO:11:

( i ) SEQUENCE CHARACTERISTICS:
        ( A ) LENGTH: 6 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:11:

Gly Gly Asn Ala Trp Leu
1                   5

( 2 ) INFORMATION FOR SEQ ID NO:12:

( i ) SEQUENCE CHARACTERISTICS:
        ( A ) LENGTH: 7 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:12:

Ser Ala Glu Ser Leu Ala Val
1                   5

( 2 ) INFORMATION FOR SEQ ID NO:13:

( i ) SEQUENCE CHARACTERISTICS:
        ( A ) LENGTH: 8 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:13:

Asn Ile Lys Asp Thr Tyr Met His
1                   5

( 2 ) INFORMATION FOR SEQ ID NO:14:

( i ) SEQUENCE CHARACTERISTICS:
        ( A ) LENGTH: 18 amino acids
        ( B ) TYPE: amino acid
        ( D ) TOPOLOGY: linear ( i i ) MOLECULE TYPE: protein ( x i ) SEQUENCE DESCRIPTION: SEQ ID NO:14:

Arg Ile Asp Pro Ala Asn Gly Asn Thr Lys Tyr Asp Pro Arg Phe Gln
1                   5                   10                  15

Gly Lys ( 2 ) INFORMATION FOR SEQ ID NO:15:

( i ) SEQUENCE CHARACTERISTICS:
        ( A ) LENGTH: 8 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:15:

Gly Gly Asn Ala Trp Leu Ala Tyr
1               5

( 2 ) INFORMATION FOR SEQ ID NO:16:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: protein ( x i ) SEQUENCE DESCRIPTION: SEQ ID NO:16:

Arg Ala Ser Gly Asn Ile His Asn Tyr Leu Ala
1               5                       10

( 2 ) INFORMATION FOR SEQ ID NO:17:

( i ) SEQUENCE CHARACTERISTICS:
        ( A ) LENGTH: 7 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:17:

Ser Ala Glu Ser Leu Ala Val
1               5

( 2 ) INFORMATION FOR SEQ ID NO:18:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: protein ( x i ) SEQUENCE DESCRIPTION: SEQ ID NO:18:

Gln Asn Phe Trp Thr Thr Pro Trp Thr
1               5

( 2 ) INFORMATION FOR SEQ ID NO:19:

( i ) SEQUENCE CHARACTERISTICS:
        ( A ) LENGTH: 35 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:19:

AAGCTTGCCG CCACCATGAA ATGCAGCTGG GTTAT        35

( 2 ) INFORMATION FOR SEQ ID NO:20:

( i ) SEQUENCE CHARACTERISTICS:
        ( A ) LENGTH: 35 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:20:

-continued

AAGCTTGCCG CCACCATGAA ATGCAGCTGG GTCAT 35

( 2 ) INFORMATION FOR SEQ ID NO:21:

( i ) SEQUENCE CHARACTERISTICS:
( A ) LENGTH: 35 base pairs
( B ) TYPE: nucleic acid
( C ) STRANDEDNESS: unknown
( D ) TOPOLOGY: unknown ( i i ) MOLECULE TYPE: DNA (genomic)

( x i ) SEQUENCE DESCRIPTION: SEQ ID NO:21:

GAAGATCTGG ATCCACTCAC CTGCAGAGAC AGTGA 35

( 2 ) INFORMATION FOR SEQ ID NO:22:

( i ) SEQUENCE CHARACTERISTICS:
( A ) LENGTH: 38 base pairs
( B ) TYPE: nucleic acid
( C ) STRANDEDNESS: unknown
( D ) TOPOLOGY: unknown ( i i ) MOLECULE TYPE: DNA (genomic)

( x i ) SEQUENCE DESCRIPTION: SEQ ID NO:22:

CTTAAGCTTG CCGCCACCAT GAGTGTGCTC ACTCAGGT 38

( 2 ) INFORMATION FOR SEQ ID NO:23:

( i ) SEQUENCE CHARACTERISTICS:
( A ) LENGTH: 36 base pairs
( B ) TYPE: nucleic acid
( C ) STRANDEDNESS: unknown
( D ) TOPOLOGY: unknown ( i i ) MOLECULE TYPE: DNA (genomic)

( x i ) SEQUENCE DESCRIPTION: SEQ ID NO:23:

CTAGATCTGG ATCCACTTAC GTTTGATTTC CAGCCT 36